(12) United States Patent
Tandiono et al.

(10) Patent No.: US 9,376,676 B2
(45) Date of Patent: Jun. 28, 2016

(54) METHOD OF BREAKING DOWN BIOLOGICAL MATERIAL

(71) Applicants: Agency for Science, Technology and Research, Singapore (SG); Nanyang Technological University, Singapore (SG)

(72) Inventors: Tandiono Tandiono, Singapore (SG); Claus-Dieter Ohl, Singapore (SG); Siak-Wei Dave Ow, Sinagpore (SG); Siew-Wan Ohl, Singapore (SG); Evert Klaseboer, Singapore (SG)

(73) Assignees: Agency for Science, Technology and Research, Singapore (SG); Nanyang Technological University, Singapore (SG)

( * ) Notice: Subject to any disclaimer, the term of this patent is extended or adjusted under 35 U.S.C. 154(b) by 240 days.

(21) Appl. No.: 14/020,106

(22) Filed: Sep. 6, 2013

(65) Prior Publication Data

US 2014/0070033 A1    Mar. 13, 2014

Related U.S. Application Data

(60) Provisional application No. 61/697,842, filed on Sep. 7, 2012.

(51) Int. Cl.
| | |
|---|---|
| *B02C 19/18* | (2006.01) |
| *C12N 13/00* | (2006.01) |
| *C12N 1/06* | (2006.01) |
| *C12M 1/00* | (2006.01) |

(52) U.S. Cl.
CPC ............. *C12N 13/00* (2013.01); *B02C 19/18* (2013.01); *C12M 47/06* (2013.01); *C12N 1/066* (2013.01)

(58) Field of Classification Search
CPC .. B02C 19/18; B02C 2019/183; C12N 13/00; C12N 1/066; C12M 47/06
USPC ............................... 241/1, 5, 18, 19, 21, 33, 2
See application file for complete search history.

(56) References Cited

U.S. PATENT DOCUMENTS

| 6,719,449 B1 * | 4/2004 | Laugharn et al. ............. 366/127 |
| 2009/0023223 A1 * | 1/2009 | Eastwood et al. ............ 436/172 |

OTHER PUBLICATIONS

Chudy et al., "Miniaturized Tools and Devices for Bioanalytical Applications: an Overview," Anal Bioanal Chem, 2009, 395:647-668.
Arora et al., "Latest Developments in Micro Total Analysis Systems," Analytical Chemistry, vol. 82, No. 12, Jun. 15, 2010, pp. 4830-4847.
Salieb-Beugelaar et al., "Latest Developments in Microfluidic Cell Biology," Analytical Chemistry, vol. 82, No. 12, Jun. 15, 2010, pp. 4848-4864.

(Continued)

*Primary Examiner* — Mark Rosenbaum
(74) *Attorney, Agent, or Firm* — Winstead, P.C.

(57) ABSTRACT

In various embodiments, a method of breaking down biological material is provided. The method may include providing a sample comprising the biological material in a liquid. The method may further include providing a gas such that the gas forms an interface with the liquid. The method may also include breaking down the biological material by applying acoustic waves in a plurality of sequential bursts to the interface.

19 Claims, 22 Drawing Sheets

(56) References Cited

OTHER PUBLICATIONS

Edlich et al., "Microfluidic Reactor for Continuous Cultivation of *Saccharomyces cerevisiae*," Biotechnol. Prog.,vol. 26, No. 5., 2010, pp. 1259-1270.
Lee et al., "Microfluidic Chemostat and Turbidostat with Flow Rate, Oxygen, and Temperature Control for Dynamic Continuous Culture," Lab on a Chip, 2011, pp. 1-10.
Boettner et al., "High-Throughput Screening for Expression of Heterologous Proteins in the Yeast *Pichia pastoris*," Journal of Biotechnology, vol. 99, 2002, pp. 51-62.
Daly et al., "Expression of Heterologous Proteins in Pichia Pastoris: a Useful Experimental Tool in Protein Engineering and Production," Journal of Molecular Recognition, vol. 18, 2005, pp. 119-138.
Schilling et al., "Cell Lysis and Protein Extraction in a Microfluidic Device with Detection by a Fluorogenic Enzyme Assay," Analytical Chemistry, vol. 74, No. 8, Apr. 15, 2002, pp. 1798-1804.
Waters et al., "Microchip Device for Cell Lysis, Multiplex PCR Amplification, and Electrophoretic Sizing," Analytical Chemistry, vol. 70, No. 1, Jan. 1, 1998, pp. 158-162.
Wang et al., "A Microfluidic Flow-Through Device for High Throughput Electrical Lysis of Bacterial Cells Based on Continuous DC Voltage," Biosensors and Bioelectronics, vol. 22, 2006, pp. 582-588.
Carlo et al., "Reagentless Mechanical Cell Lysis by Nanoscale Barbs in Microchannels for Sample Preparation," Lab Chip, vol. 3, 2003, pp. 287-291.
Kim et al., "Cell Lysis on a Microfluidic CD (Compact Disc)," Lab Chip, vol. 4, 2004, pp. 516-522.
Jha et al., "Electrochemical Cell Lysis on a Miniaturized Flow-Through Device," Current Applied Physics, vol. 9, 2009, pp. e301-e303.
Taylor et al., "Lysing Bacterial Spores by Sonication Through a Flexible Interface in a Microfluidic System," Analytical Chemistry, vol. 73, No. 3, Feb. 1, 2001, pp. 492-496.
Bigelow et al., "The Destruction of *Escherichia coli* Biofilms Suing High-Intensity Focused Ultrasound," Ultrasound in Med. & Biol., 2009, pp. 1-6.
Le Gac et al., "Sonoporation of Suspension Cells with a Single Cavitation Bubble in a Microfluidic Confinement," Lab Chip, vol. 7, 2007, pp. 1666-1672.
Tandiono et al., "Creation of Cavitation Activity in a Microfluidic Device Through Acoustically Driven Capillary Waves," Lab Chip, vol. 10, 2010, pp. 1848-1855.
Lee et al., "Quantitative Real-Time Polymerase Chain Reaction for Determination of Plasmid Copy Number in Bacteria," Journal of Microbiological Methods, vol. 26, 2006, pp. 258-267.
Wang et al., "Effects of the Presence of ColEl Plasmid DNA in *Escherichia coli* on the Host Cell Metabolism," Microbial Cell Factories, vol. 5, No. 34, Nov. 17, 2006, pp. 1-18.
Nordstrom et al., "Copy-Number Control of the *Escherichia coli* Chromosome: A Plasmidologist's View," EMBO Reports, vol. 7, No. 5, 2006, pp. 484-489.
Chalfie et al., "Green Fluorescent Protein as a Marker for Gene Expression," Science, vol. 263, Feb. 11, 1994, pp. 802-805.
Tsien, "The Green Fluorescent Protein," Annu. Rev. Biochem., vol. 67, 1998, pp. 509-544.
Braun, "Molecular Organization of the Rigid Layer and the Cell Wall of *Escherichia coli*," Journal of Infectious Diseases, vol. 128, Jul. 1973, Supplement, one page.
Klis, "Review: Cell Wall Assembly in Yeast," Yeast, vol. 10, 1994, pp. 851-869.
Spinorakutara, "Determination of Yeast Cell Wall Thickness and Cell Diameter Using New Methods," Journal of Fermentation and Bioengineering, vol. 86, No. 3, 1998, pp. 253-260.
Tandiono et al., "Sonochemistry and Sonoluminescence in Microfluidics," PNAS, vol. 108, No. 15, Apr. 12, 2011, pp. 5996-5998.
Tandiono et al., "Sonolysis of *Escherichia coli* and Pichia Pastoris in Microfluidics," Lab Chip, vol. 12, 2012, pp. 780-786.

\* cited by examiner

FIG. 1

100 providing a sample comprising the biological material in a liquid ⟵ 102 providing a gas such that the gas forms an interface with the liquid ⟵ 104 breaking down the biological material by applying acoustic waves in a plurality of sequential bursts to the interface ⟵ 106

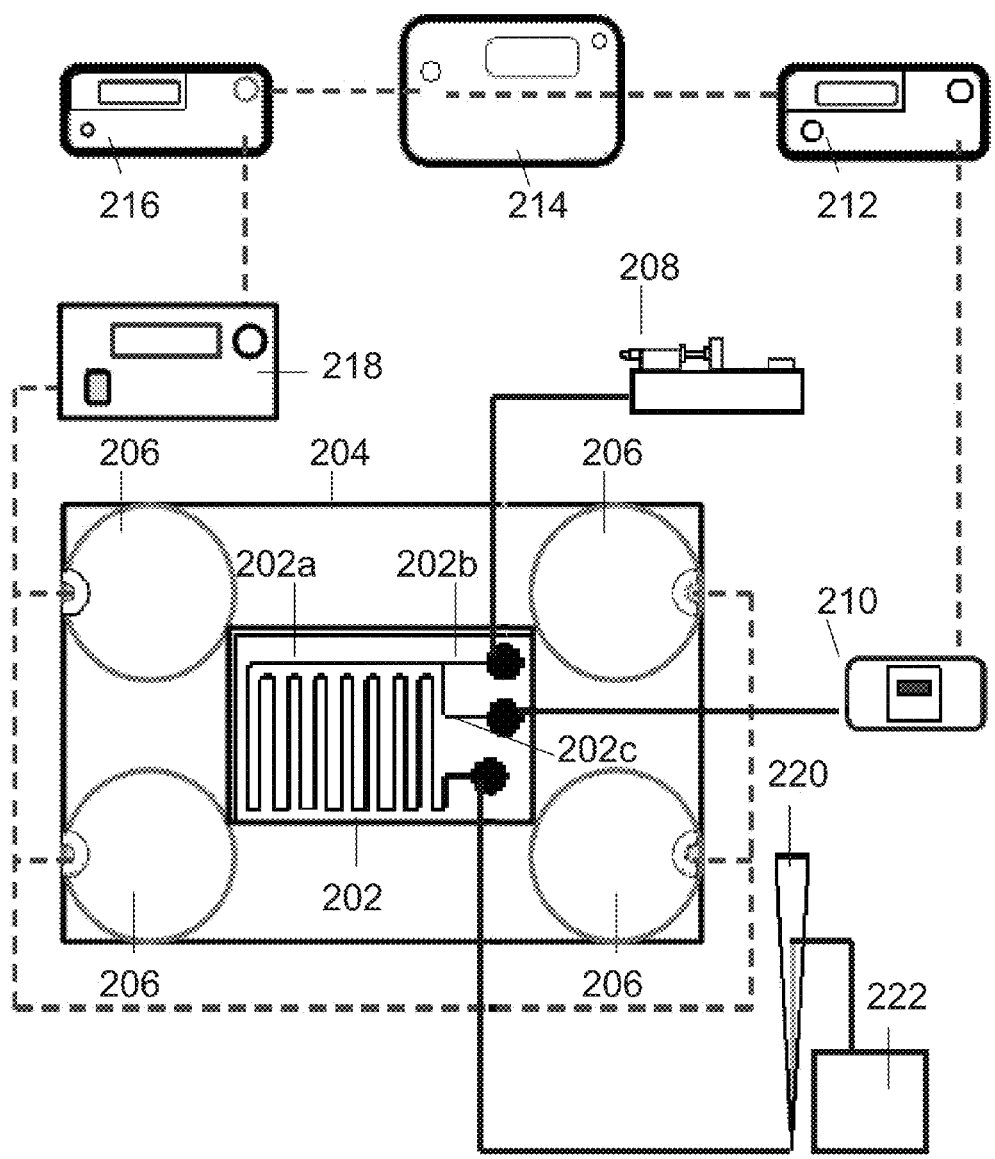

300a

300b

300c

400a

400b

METHOD OF BREAKING DOWN BIOLOGICAL MATERIAL

CROSS-REFERENCE TO RELATED APPLICATIONS

This application claims the benefit of priority of U.S. provisional application No. 61/697,842 filed Sep. 7, 2012, the contents of it being hereby incorporated by reference in its entirety for all purposes.

TECHNICAL FIELD

Various aspects of this disclosure relate to method of breaking down biological materials such as cells and endospores.

BACKGROUND

Micro-scale analysis of intracellular contents, such as nucleic acids and proteins, is gaining importance in biology. Other than enabling minimized analytical and cell biology profiling of processes at the cellular level, microfluidics is also finding new applications relating to micro-culturing of cells for high throughput screening and biological research. The prokaryotic Gram-negative *Escherichia coli* bacterium and the eukaryotic *Pichia pastoris* yeast are microbial host cells extensively used for screening of clones from genomic libraries and heterologous protein expression. They both allow the parallel functional expression of multiple proteins in microplate assays, which may be made amendable to micro-scale analysis. However, before the micro-scale analysis can be carried out, an effective microfluidic cell lysis for the release of active intracellular contents needs to be achieved.

In microfluidics, cell lysis may be accomplished by chemical, thermal, electrical, or mechanical means. Of these, chemical lysis with lytic agents and thermal lysis with heat frequently lead to the denaturation of proteins or interfere with subsequent assays. Furthermore, chemical lysis has the added disadvantages of requiring wet chemical storage and intensive mixing, which may add complexity in a microfluidic setting. Although electrical cell lysis may have the advantages of being reagent-less and quick, the application of a direct current at elevated voltage may lead to water hydrolysis, undesirable localized heating, and/or denaturation of proteins. Mechanical lysis, which may involve the generation of high shear through the application of high pressure, rapid agitation, or sonication, often needs intensive cooling to remove the heat produced by the dissipation of the mechanical energy.

Despite the disadvantages of undesirable heating, sonication has been widely used in lab-scale settings to attain mechanical lysis of cells. The basic principle of sonication is to generate mechanical shear stress by oscillating cavitation bubbles using an ultrasound field. In bulk medium, this typically involves the application of a bench-top vibrating probe directly into the liquid. The rapid movement of the probe tip creates a series of rapidly collapsing cavitation bubbles that break apart cells. This process may inefficient and some energy may be lost as heat.

SUMMARY

In various embodiments, a method of breaking down biological material is provided. The method may include providing a sample comprising the biological material in a liquid. The method may further include providing a gas such that the gas forms an interface with the liquid. The method may also include breaking down the biological material by applying acoustic waves in a plurality of sequential bursts to the interface.

BRIEF DESCRIPTION OF THE DRAWINGS

The invention will be better understood with reference to the detailed description when considered in conjunction with the non-limiting examples and the accompanying drawings, in which:

FIG. 1 shows a flow chart of a method according to various embodiments.

FIG. 2A shows a schematic of a setup according to various embodiments.

FIGS. 7A-F are a high speed sequence of images showing the deformation and disruption of the yeast cells when they are exposed to the US vibration; wherein FIG. 7A is an image including a group of cells just prior to ultrasound (US) exposure; wherein FIG. 7B is an image of the group of cells 10 μs since ultrasound (US) exposure; wherein FIG. 7C is an image of the group of cells 20 μs since ultrasound (US) exposure; wherein FIG. 7D is an image of the group of cells 30 μs since ultrasound (US) exposure; wherein FIG. 7E is an image of the group of cells 40 μs since ultrasound (US) exposure; and wherein FIG. 7F is an image of the group of cells 50 μs since ultrasound (US) exposure.

DETAILED DESCRIPTION

Figure 2B:
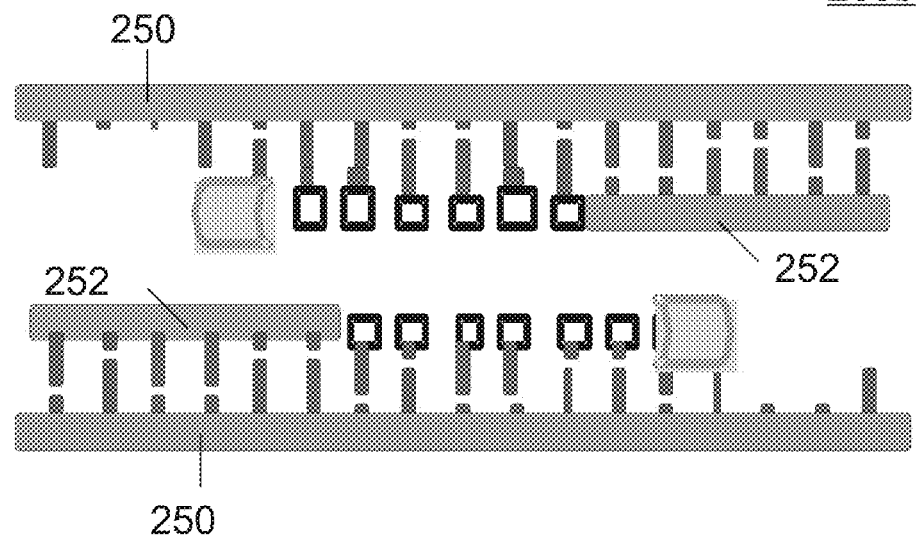
FIG. 2B shows a schematic of a quantitative real time polymerase chain reaction (qRT-PCR) analysis according to various embodiments.

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

In order that the invention may be readily understood and put into practical effect, particular embodiments will now be described by way of examples and not limitations, and with reference to the figures.

FIG. 1 shows a flow chart 100 of a method according to various embodiments. In various embodiments, the method may include, in 102, providing a sample comprising the biological material in a liquid. The method may further include, in 104, providing a gas such that the gas forms an interface with the liquid. The method may also include, in 106, breaking down the biological material by applying acoustic waves in a plurality of sequential bursts to the interface.

In other words, the method may include allowing a liquid containing the biological material to form an interface with a gas. The method may further include applying acoustic waves to the interface to break down the biological material. The acoustic waves may be applied in a plurality of sequential bursts.

In various embodiments, cavitations may be generated by oscillations when the acoustic waves are applied to the interface. The cavitations may be configured to break down the biological material. The cavitations may be intense cavitations.

Various embodiments provide a convenient method to break down biological material, e.g. cell lysis, by applying acoustic waves to a liquid-gas interface to generate intense cavitation. The method may break down biological material without requiring additional material or consumables such as beads or chemical reagents. Various embodiments may allow sonication of volumes of samples without direct contact between transducers and samples, hence reducing the possibility of assay interference or sample cross-contamination. In various embodiments, the acoustic waves such as ultrasound may be applied in a plurality of bursts for a brief duration with minimal heating, hence facilitating functional downstream characterization of biological fragments such as nucleic acids and proteins in microfluidics.

In various embodiments, providing the sample may include providing the sample via any suitable means such as flowing the sample through an inlet channel or an inlet pipe. In various alternative embodiments, the sample may be provided in a microwell or an array of microwells. In various embodiments, providing the gas may include providing the gas via any suitable means such as flowing the gas through a further inlet channel or a further inlet pipe.

For instance, the sample containing the biological material may be flowed through an inlet channel of a microfluidic device. The gas may be flowed through a further inlet channel of the microfluidic device. The inlet channel and further inlet channel may be connected such that the sample and the gas may contact each other to form a gas-liquid interface.

In various alternate embodiments, the sample may be provided in an array of microwells. The gas may be brought into contact with the sample via a pipe or channel.

The cavitations may be generated by nonlinear oscillations of gas-liquid interfaces when the acoustic waves are applied to the interface. The cavitations may be configured to break down the biological material. Cavitations may be also referred to as cavitation bubbles or bubbles or voids. Cavitations may be vapour cavities formed in liquid-free zones that are the consequence of forces acting upon the liquid. An oscillating liquid-gas interface may generate stable cavitations. In various embodiments, the method may include controlling the cavitations formed by controlling the duration in which acoustic waves are applied to the interface. By controlling the cavitations, the biological material may be broken down without excessive heating.

The acoustic waves may be generated by one or more piezoelectric transducers. The acoustic waves may be ultrasound waves. In various embodiments, ultrasound waves may be at the resonance frequency of a microfluidic system. In various embodiments, intense cavitations may be generated in a microfluidic channel by exciting the gas-liquid interface. The cavitations may induce liquid shear for breaking down the biological material, such as lysing cells.

The cavitations may be initiated from a nonlinear interface instability that entraps small gas bubbles. The small gas bubbles may later serve as cavitation nuclei. Cavitation nuclei are minute stabilized gas bodies upon which cavitations grow. Cavitation nuclei may be necessary as acoustic cavitation is a heterogeneous phenomenon which is initiated from weak spots in the liquid. Cavitations nuclei are stabilized gas bubbles in crevices of particles or surfaces, and may be naturally present in most aqueous liquids unless filtered to utmost purity. However, in microfluidic devices, little opportunity is given for the stabilization of gaseous bubbles, as typically the surfaces of glass and PDMS are clean. Furthermore, the static pressure within the channels is normally high (leading to a fast dissolution of gas bubbles) and the volume of liquid is very small. Thus, acoustic cavitation which relies on nuclei is unlikely to occur in microfluidics—even at very high acoustic pressures—unless they are introduced artificially.

Various embodiments may be able to generate cavitation nuclei by applying acoustic waves to oscillate the liquid-gas interface. When the air-liquid interface is oscillated by the acoustic waves, standing capillary waves may be excited on the interface. A capillary wave is a wave travelling on the surface of a liquid where the restoring force is provided by the interfacial tension, i.e. for sufficient short wavelengths to ignore gravity. Then the relation between the wavelength $\lambda$ and the oscillation frequency $f_{cap}$ in the absence of viscosity is given by the dispersion equation (Equation 1):

$$\lambda = \left(\frac{2\pi\sigma}{f_{cap}^2 \rho}\right)^{1/3} \quad (1)$$

Where $\sigma$ is the coefficient of interfacial tension and $\rho$ is the density of the liquid.

Application of the acoustic waves may cause standing waves to be formed on the liquid-gas interface. The surface may oscillate periodically at half the driving frequency. The amplitude of oscillation may increase when the driving voltage is increased. Wave crests at the liquid-gas interface may become more pointed while troughs only slightly increase in amplitude. Increasing the driving voltage may further leads to a jetting of the crests into the gas and Rayleigh-Plateau instability and the eventual formation of droplets. At sufficiently high driving amplitude, small bubbles may be entrapped between neighboring and coalescing crests. When the coalescing crests recede, the bubbles formed may move away from the interface.

In various embodiments, the biological material may be cells. The biological material may be broken into biological material fragments. For instance, the cell membrane and/or the cell walls of cells may be ruptured to release biological material fragments such as intracellular deoxyribonucleic acids (DNAs), intracellular proteins and cytoplasmic material or molecules. Biological material may also include tissues, bacteria, viruses, yeast or bacterial endospores etc. The biological material may be living or dead. The oscillations of the cavitations may create regions of high stress, which may rupture parts of the biological material, e.g. cell membranes and/or the cell walls of cells, if the cavitations are sufficiently close to the biological material. Biological material fragments may include intracellular contents of cells.

In various embodiments, the method may further include detecting the biological material fragments. Detection may be done using a suitable fluorescence intensity measurement method. In various embodiments, detecting the biological material fragments may include introducing green fluorescence protein (GFP) genes into the biological material such as cells. Florescence emission by the GFP genes may be detected using fluorescence microscopy. The method may include detecting the GFP genes after the GFP genes are introduced into the biological material but before generation of the acoustic waves. The method may additionally or alternatively include detecting the GFP genes after or during generation of acoustic waves. Breaking down of the biological material such as rupture of cells may release biological material fragments with GFP genes. The amount or concentration of biological material fragments may be detected or measured by detecting the amount of fluorescence emitted upon excitation.

Additionally or alternatively, detecting the biological material fragments may include quantitative real time polymerase chain reaction (qRT-PCR) analysis to detect and/or measure the biological material fragments such as intracellular DNA. Quantitative real time polymerase chain reaction (qRT-PCR) analysis may be carried out in a thermal cycler. qRT-PCR may include amplifying the biological material fragments such as DNA. qRT-PCR may further include determining the amount or concentration of biological fragments by using a binding dye or flurochrome. The binding dye or flurochrome may bind to a specific sequence in the biological material fragments. The method may include exciting the binding dye or flurochrome and detecting the emission of the binding dye or flurochrome. The method may further include determining the amount or concentration of biological fragments based on the intensity of the emitted florescence.

In various embodiments, the method may additionally or alternatively include detecting intact biological materials after applying acoustic waves. The biological materials that have been broken down may be determined based on the intact biological materials. Detecting intact biological materials may include plate count.

The interface may be formed in a main channel of a microfluidic device. Providing the sample may include flowing the sample through an inlet channel, the inlet channel in connection with the main channel. Providing the gas may include flowing the gas through a further inlet channel, the further inlet channel in connection with the channel.

In various embodiments, a microfludic device may be provided. The microfluidic device may include a main channel. The main channel may be coupled or connected to an inlet channel. The main channel may also be further coupled or connected to a further inlet channel. In various embodiments, the inlet channel may be configured to carry the sample. The inlet channel may be coupled to a pump such as a syringe pump. The pump may be configured to pump the sample into the inlet channel. In various embodiments, the further inlet channel may be configured to carry the gas. A pressure controller may be coupled to the further inlet channel. The pressure controller may be configured to control the pressure in the main channel. In various embodiments, a method of using the microfluidic device to break down biological material may be provided. The method may include flowing a sample through an inlet channel of the microfluidic device. The sample may include a biological material in a liquid. The method may further include flowing a gas through a further inlet channel. The inlet channel and the further inlet channel may be connected. The sample and the gas may form an interface. The method may further include breaking down the biological material by applying acoustic waves to the interface. Cavitations may be generated by oscillations when the acoustic waves are applied to the interface. The cavitations may be configured to break down the biological material.

In various embodiments, the inlet channel may at least be at least substantially perpendicular to the further inlet channel. The main channel, the inlet channel and the further channel may form a T-junction. For instance, the inlet channel and the main channel may be continuous along a straight line. The further inlet channel may meet the inlet channel and the main channel at about 90 degrees to form the T-junction. In various alternate embodiments, the main channel, the inlet channel and the further channel may form a Y-junction.

In various embodiments, the main channel may include a meandering portion or a spiral portion. In various embodiments, total length of the main channel may be about 100 mm to about 1000 mm, e.g. about 500 mm. In various embodiments, the main channel may have a width of about 50 μm to about 1000 μm, e.g. about 500 μm. The main channel may have a height of about 10 μm to about 30 μm, e.g. 20 μm.

In various embodiments, the inlet channel may have a width of about 50 μm to about 200 μm, e.g. about 100 μm. The inlet channel may have a height of about 10 μm to about 30 μm, e.g. 20 μm. In various embodiments, the further inlet channel may have a width of about 20 μm to about 100 μm, e.g. about 50 μm. The further inlet channel may have a height of about 10 μm to about 30 μm, e.g. 20 μm.

The main channel may be connected to a collection tube through an outlet. The collection tube may be configured to minimize evaporation of the liquid. The liquid may also be referred to as the supernatant. Tandiono et. al. (*Lab Chip,* 2010, 10, 1848-1855) provides the details of the microfluidic device and the method of fabricating the microfluidic device and is herein incorporated by reference in its entirety for all purposes.

In various embodiments, the transducers may be isolated from the gas or sample flowing in the main channel, the inlet channel and the further inlet channel. Advantageously, isolation of the transducers from the channels removes the need to integrate the transducers into the microfluidic device and reduces complexity and costs during fabrication of the microfluidic device.

In various embodiments, the ability to introduce strongly oscillating cavitations in a microfluidic setting without localized heating may offer an unparallel potential for reagent-less cell lysis without protein denaturation, hence facilitating lab-on-chip analysis.

In various embodiments, the method may include increasing pressure of the gas to flush the biological material fragments. The pressure of the gas may be increased for a time interval of about 1 to about 30 seconds or about 5 to about 10 seconds. The method may further include decreasing the pressure of the gas after flushing the sample including the biological material fragments. When the microfluidic device described above is used, the pressure of the gas may be increased or decreased using the pressure controller. In various embodiments, the pressure of the gas before flushing the biological material fragments may be at a first pressure. The pressure may be increased to a second pressure to flush the biological material fragments to a collector such as the collection tube. After the time interval, the pressure of the gas may be decreased to a third pressure. The third pressure may be substantially equal to the first pressure or may be lower than the first pressure.

The method may further include flowing a subsequent sample including a subsequent biological material after flushing the sample including the biological material fragments. The subsequent biological material may be the same type of biological material or a different type of biological material.

In various embodiments, the plurality of sequential bursts may be applied for less than about a minute or less than about 40 s or less than about 35 s or from about 20 s to about 35 s or from about 30 s to about 32 s or about 30 s or about 31 s or about 32 s. A first burst of the plurality of sequential bursts may be separated from a second burst of the plurality of sequential bursts by a time interval. The time interval may be about 3 to about 10 seconds or about 4 to about 9 seconds or about 5 to about 8 seconds or about 5 seconds or about 6 seconds. In various embodiments, the time intervals between sequential bursts may be substantially the same. In various embodiments, the plurality of sequential bursts may be 1 to 100 bursts or 5 to 70 bursts or 5 to 65 bursts. In various embodiments, the acoustic waves may be at a predetermined fixed frequency. In other words, the bursts of acoustic waves may have the same frequency. In various embodiments, the acoustic waves may be at a resonance frequency of the setup for performing the method. The acoustic waves may be at a resonance frequency of the microfluidic device. The resonance frequency of the setup or microfluidic device may be determined prior to performing the method. The resonance frequency of setup or microfluidic device may be determined by varying the driving frequency and measuring the radiofrequency (RF) power. The resonance frequency may be the driving frequency when RF power reaches a maximum. In various embodiments, the plurality of sequential bursts of acoustic waves may be applied to the interface such that the temperature increase of the microfluidic device does not exceed 5° C. or does not exceed 4° C. or does not exceed 3.5° C.

In various embodiments, providing the gas or flowing the gas may be controlled by a control system. Additionally or alternatively, applying the acoustic waves may be controlled by the control system. In various embodiments, the control system may be automatic and does not require human intervention when performing the method. The control system may include a circuit. The control system may be configured to follow predetermined steps of applying acoustic waves, followed by flowing the gas to flush the biological material fragments. In various embodiments, providing the sample or flowing the sample may also be controlled by the control system. The control system may be configured to control the flow rate of the sample. In various embodiments, the control system may control the flow rate by controlling the pump.

In various embodiments, a "circuit" may be understood as any kind of a logic implementing entity, which may be special purpose circuitry or a processor executing software stored in a memory, firmware, or any combination thereof. Thus, in various embodiments, a "circuit" may be a hard-wired logic circuit or a programmable logic circuit such as a programmable processor, e.g. a microprocessor (e.g. a Complex Instruction Set Computer (CISC) processor or a Reduced Instruction Set Computer (RISC) processor). A "circuit" may also be a processor executing software, e.g. any kind of computer program, e.g. a computer program using a virtual machine code such as e.g. Java.

FIG. 2A shows a schematic 200a of a setup according to various embodiments. The setup may include a microfluidic device 202. The microfluidic device 202 may include a main channel 202a. The microfludic device 202 may further include an inlet channel 202b and a further inlet channel 202c. The inlet channel 202b may be substantially perpendicular to the further inlet channel 202c. The inlet channel 202c may be coupled to the main channel 202a along a straight line. In other words, the main channel 202a, the inlet channel 202b and the further inlet channel 202c may form a T-junction. The inlet channel 202b may be configured to transport sample including biological material in a liquid to the main channel 202a. The further inlet channel 202c may be configured to carry gas to the main channel to form a liquid-gas interface. The main channel 202a, the inlet channel 202b and the further inlet channel202c may be on a substrate 204. The substrate 204 may be a glass substrate. In various alternate embodiments, the substrate 204 may include silicon or polydimethylsiloxane (PDMS).

One or more transducers 206, may also be on the substrate 204. The transducers 206 may be piezoelectric transducers such as lead zirconate titanate (PZT) transducers. The one or more transducers 206 are configured to emit acoustic waves such as ultrasound waves upon application of a potential difference.

In various embodiments, the inlet channel 202b may be coupled to a pump 208 such as a syringe pump. The pump 208 may be configured to pump samples into the inlet channel 202b. The further inlet channel 202c may be coupled to a pressure controller 210. The pressure controller 210 may be coupled to a function generator 212. The pressure controller 210 may be controlled by the function generator 212. The function generator 212 may be controlled by a pulse/delay generator 214.

The pulse/delay generator 214 may also control another further function generator 216. The further function generator 216 is coupled to an amplifier 218 via a suitable means such as an electrical connection. The amplifier 218 is coupled to the one or more transducers 206. The pressure generator 210, the function generator 212, the pulse/delay generator 214, the further function generator 212 and the amplifier 218 may form the control system. In various embodiments, the control system may control the flow of samples through the main channel 202a and the application of acoustic waves. The control system may follow a computer algorithm or program to control the flow of samples through the main channel 202a and the application of acoustic waves.

The main channel 202a may be connected to a collection tube 220 through an outlet. The collection tube 220 may be coupled to an assay system 222. In various embodiments, the assay system 222 may be an off-line assay system such as quantitative real time polymerase chain reaction (qRT-PCR) analysis, fluorescence intensity measurement and/or plate count.

In various embodiments, at least a portion of the setup may be an integrated device. The integrated device may for instance include the microfluidic device 202. The integrated device may further include the assay system 222 and/or the at least one transducers 206.

Figure 2C:
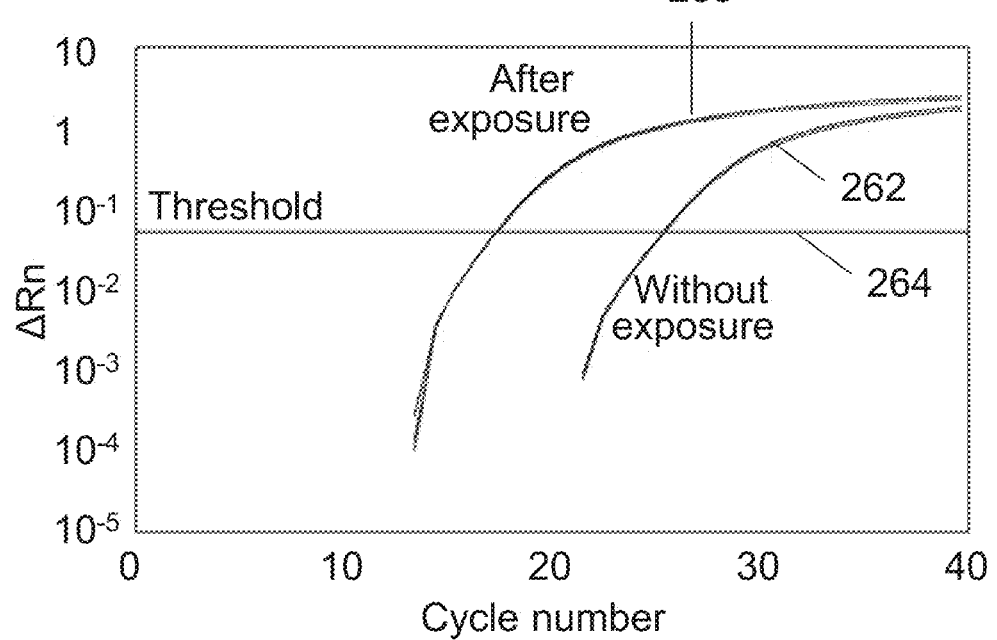
FIG. 2C shows a graph of detected DNA fluorescence ($\Delta R_n$) as function of cycle number.

FIG. 2B shows a schematic 200b of a quantitative real time polymerase chain reaction (qRT-PCR) analysis according to various embodiments. Quantitative real time polymerase chain reaction (qRT-PCR) analysis may be carried out in a thermal cycler. A pair of primers may be used to amplify biological material fragments such as DNA or messenger ribonucleic acids (mRNA). A binding dye or flurochrome 252 such as SYBR® Green may be used to bind to separated DNA or RNA strands 250. The dye or flurochrome 252 may be excited by light of a specific wavelength to emit fluorescence. The thermal cycler may include one or more sensors to detect the fluorescence emitted by the excited dye or flurochrome. FIG. 2C shows a graph 200c of detected DNA fluorescence ($\Delta R_n$) as a function of cycle number. Line 260 shows the results obtained when ultrasound is applied to break down the cells. Line 262 shows the results obtained when ultrasound is not applied. The DNA detected increases upon application of ultrasound. Line 264 represents the threshold line used in qRT-PCR to calculate DNA concentration. The interception of line 264 with the qRT-PCR readings (also known as the Ct value) of lines 260 and 262 is inversely proportional to DNA concentration.

In an example, a meandering microfluidic main channel 202a and four PZT material disc transducers 206 with 20 mm diameter and 2.1 mm thickness (Steiner & Martins) are used. The transducers are attached to a glass substrate 204. The microfluidic device is formed on polydimethylsiloxane (PDMS). It consists of two inlet channels 202b, 202c and one outlet. Each of the inlet channels 202b, 202c is coupled to an inlet. The inlet channels are connected through a T junction such that the gas may be injected to the main channel 202a to create gas-liquid interfaces within the main channel 202a. The width of the gas channel 202c is 50 μm and the widths of channels 202a, 202b are 100 μm. The main channel 202a expands to 500 μm downstream to achieve shorter gas/liquid slugs and thus longer interfaces in the channel 202a. The height of the channel 202a is 20 μm. The outlet of the channel 202c is connected to a collection tube 220. The tube 220 is specially designed to minimize evaporation of the supernatant.

Figure 2D:
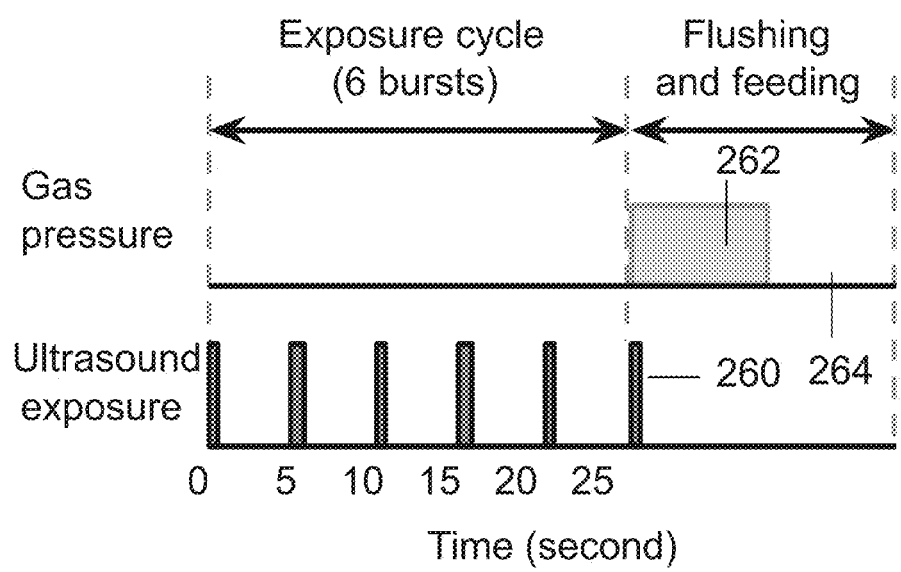
FIG. 2D is a timing diagram illustrating the timings of the acoustic wave exposure and the flushing of the channel at the end of the cycle.

The ultrasound exposures and the gas pressure injected into the microchannel 202a are run by an automatic control system. FIG. 2D is a timing diagram 200d illustrating the timings of the acoustic wave exposure and the flushing of the channel 202a at the end of the cycle. For each cycle, the sample may be exposed to six bursts of ultrasound. At the end of each cycle, the sample in the channel 202a is flushed out by applying higher pressure gas pressure. The total duration of a full cycle ($t_{cyc}$) may vary between 32-45 seconds, depending on the flushing and feeding duration.

A syringe pump 208 pushes the sample liquid at a constant flow rate. The sample is exposed to six bursts of ultrasound every 5 seconds by an amplifier 218 (AG1021, LF Amplifier/Generator, T&C Power Conversion). This time interval of 5 seconds allows the sample to cool down. Each burst may be composed of a harmonic driving of about 500 to about 50 000 ultrasound cycles with about amplitude of about 200 V at the resonance frequency of the microfluidic system. The driving amplitude may be chosen such that intense cavitation always occurs when the microfluidic system is exposed to the ultrasound. The amplitudes of the acoustic pressure inside the microchannel 202a and displacement of the glass substrate 204 at this driving amplitude were measured to be approximately 10 bars and 0.4 μm, respectively. The resonance frequency was determined prior to the experiments by adjusting the driving frequency of the amplifier 218 such that the power delivered to the system is at its maximum. The frequency alters slightly with each device by a few kilohertz; on average it is around 130 kHz. The total duration of the ultrasound exposure may be varied between tens of milliseconds to seconds. The exposed sample is subsequently flushed out to the collection tube 220 by applying a high pressure 262 to the gas inlet channel 202c for about 5 to about 10 seconds, followed by about 5 to about 20 seconds of reduced pressure 264 for the flow in the channel 202a to stabilize and fresh sample to be injected into the channel 202a. The automatic control system then starts a new cycle. The amplifier 218 and pressure controller 210 (VSO-BT Benchtop Controller, Parker, USA) are timed by function generators 212, 216 (33220A 20 MHz Function/Arbitrary Waveform Generator, Agilent Technologies, USA) which are triggered by a digital delay generator 214 (Model 575, BNC, USA).

Fabrication of the microfluidic device followed standard soft lithography techniques. A commonly used epoxy-based negative photoresist (SU-8 2050, MicroChem) was spun to form a 20 mm film thickness on a 50×75 $mm^2$ microscope slide. After pre-exposure bake (soft bake), the substrate was exposed to UV-light on a mask aligner (Manual Mask Aligner MJB4, SUSS Micro-Tec), subsequently followed by post-exposure bake. The development process was then performed by immersing the substrate into SU-8 Developer. The patterned substrate was used as a master to cast a microfluidic device in PDMS (Sylgard 184 Silicone Elastomer Kit, Dow Corning). The resulting microfluidic device was then bonded onto a microscope slide using a plasma cleaner (Expanded Plasma Cleaner PDC-002, Harrick Plasma). A piezoelectric transducer (PZT material, disc transducer: 25 mm diameter with 2.1 mm thickness, Steiner & Martins) was glued onto the same microscope slide, next to the device, using a very thin layer of epoxy glue.

The microbial strains used for quantitative real time polymerase chain reaction (qRT-PCR) analysis were green fluorescence protein (GFP) expressing *Escherichia coli* BL21 (DE3) and *Pichia pastoris* GS990 strains harbouring the pAcGFP1 (Clontech) and pGAP-EGFPd vectors respectively. *Escherichia coli* and *Pichia pastoris* were chosen because they are widely used for screening of cDNA genomic libraries and functional protein expression. The cell concentration of the samples was maintained constant at an optical density measured at 600 nm ($OD_{600}$) of approximately 4.0 and 7.0 for *E. coli* and *P. pastoris*, respectively. Cell suspension at a volume of 60-100 μl was fed into the microchannel for ultrasound treatment. The treated samples were collected in a collection tube, and centrifuged (13 000 rpm, 1 min) to collect the supernatant. As the cells lysed, intracellular proteins and nucleic acids would be released into the supernatant and can be subsequently measured based on GFP fluorescent and qRT-PCR analyses.

The GFP fluorescence intensity measurement of the *E. coli* was performed on a microplate reader (Infinite 200, Tecan, Switzerland). Treated and untreated samples were diluted two times in tris-buffered saline buffer and placed on a microplate (Greiner 96 Flat Bottom Black Polystyrol, Germany) according to the manufacturer's protocol. The excitation and emission wavelengths used in the measurement were 475 nm and 509 nm, respectively, which correspond to the maximum excitation and emission peaks of the wildtype GFP variant expressed in the experiments.

Figure 2E:
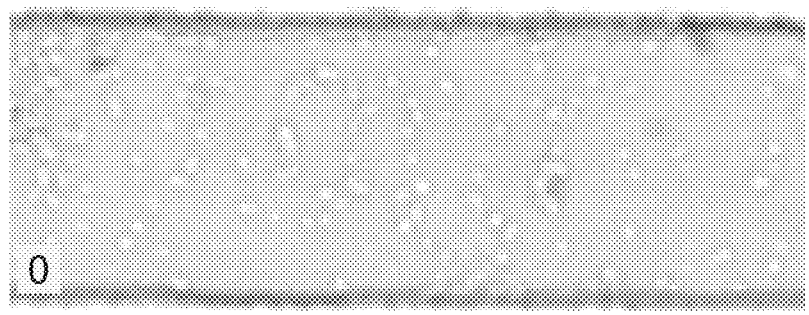
FIG. 2E is a photo of the main channel filled with yeast cells before application of ultrasound waves.
Figure 2F:
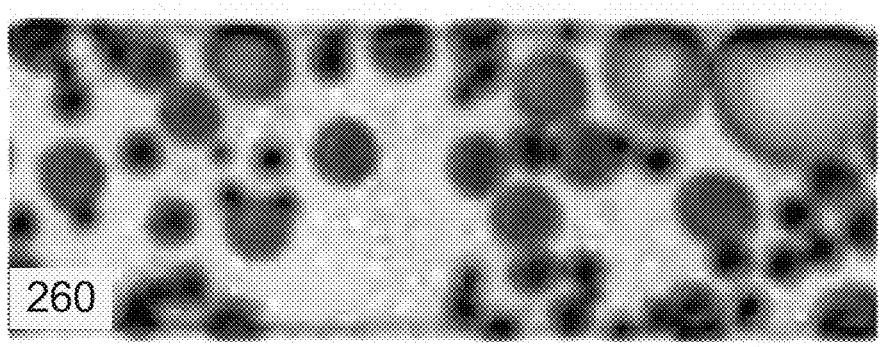
FIG. 2F is a photo of cavitations formed in the main channel upon application of ultrasound waves.
Figure 2G:
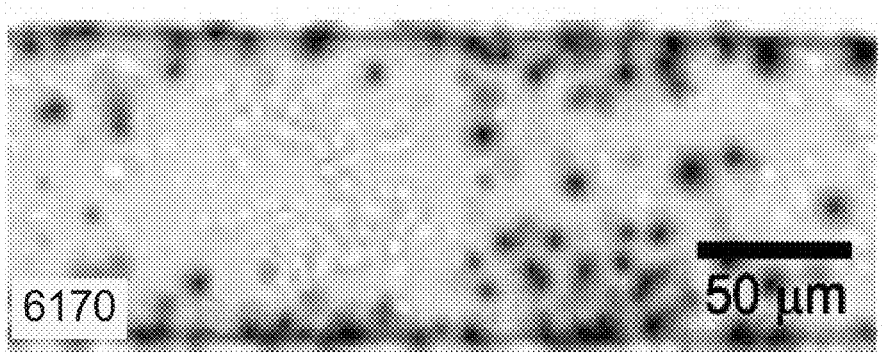
FIG. 2G is a photo of the main channel of the collapsing of the cavitations.

The qRT-PCR assay was conducted on an ABI PRISM 7500 instrument (Applied Biosystems, California, USA) to quantify the release of intracellular DNA from lysed cells according to a modified protocol from Lee et al. (*J. Microbiol. Methods* 2006, 65, 258-267). The assay was performed with the following cycling conditions: 50° C. for 2 min, 95° C. for 10 min, and followed by 40 cycles of 95° C. for 15 s and 60° C. for 1 min each. Each 25 µl PCR reaction contains 2 µl of standard or sample DNA, 12.5 µl of SYBRR Green PCR Master Mix (Applied Biosystems), 9.25 µl water, and 12.5 pmol each of forward and reverse primers (*Pichia* 18SrDNA primer-1 ATTACGTCCCTGCCCTTTGTAC, *Pichia* 18 SrDNA primer-2 CCAAAGCCTCACTAAACCATTCA, *E. coli* 16SrDNA primer-1 TCGTGTTGTGAAATGTTGGGTTA, *E. coli* 16SrDNA primer-2 CCGCTGGCAACAAAGGATA). Serial dilutions of *E. coli* or *P. pastoris* genomic DNA standards were run in duplicate to establish the standard curves of PCR threshold cycle (Ct) versus log DNA concentration (Co). From these, the interpolation of the Ct value against the standard curve would allow the quantification of total DNA presented in samples. The theoretical DNA yield was calculated based on a DNA content of 3.1% for cells with a single copy of chromosome and an average 2-4 copies of chromosome per dividing cell. As an OD 4.0 culture corresponds to approximately 2 g cells/l (1 OD=0.5 g dry cell mass/l), the theoretical DNA yield is estimated to be around 124-248 ng/µl. A camera (Fastcam SA1.1, Photron, Japan) connected to an inverted microscope (IX-71, Olympus, Japan) is used for high-speed imaging at up to 300 000 frames/s. FIG. 1C shows selected frames from a sequence showing yeast cells in a microchannel with an exposure time of 1 µs. FIG. 2E is a photo 200e of the main channel 202a filled with yeast cells before application of ultrasound waves. FIG. 2F is a photo 200f of cavitations formed in the main channel 202a upon application of ultrasound waves. FIG. 2G is a photo 200g of the main channel 202a of the collapsing of the cavitations.

Green fluorescence protein (GFP) from jellyfish *Aequorea Victoria* is a well-established reporter protein for functional gene expression studies in bacteria, yeast, and several other organisms. For quantifying the effectiveness of the cell lysis method and for imaging purposes, the GFP gene was cloned under the control of a constitutive promoter and introduced into *E. coli* and *P. pastoris*.

The cell wall of the Gram-negative bacterium *E. coli* includes a single layer of peptidoglycan surrounded by an outer membrane. The outer membrane is composed of lipopolysaccharides, lipoproteins, and phospholipids. The disruption of the cell wall requires the destruction of the thin layer of the peptidoglycan network with an approximately 10 nm thickness. The diameter of the cavitation bubbles at maximum expansion (see for example FIG. 2F) is much larger than the typical length of *E. coli*, i.e. 4-6 µm. However, during the collapse phase, the bubbles shrink below the resolution limit of the camera, thus the fluid mechanic cavitational force on the bacteria may occur on scales comparable to the bacterial size.

Figure 3A:
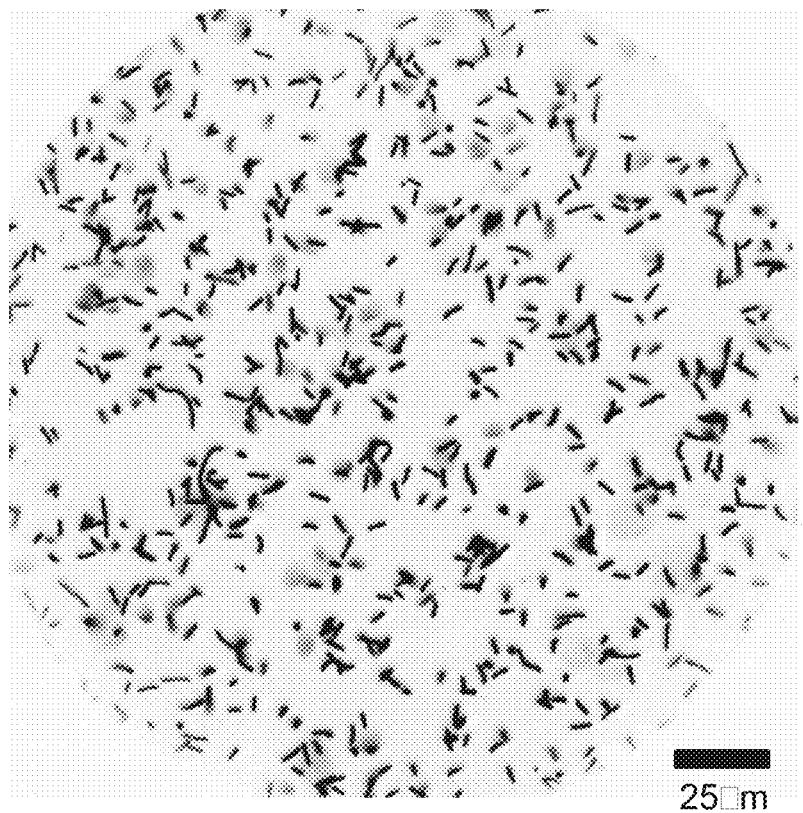
FIG. 3A is an image depicting the green fluorescence protein (GFP) emission before ultrasound exposure using florescence microscopy.
Figure 3B:
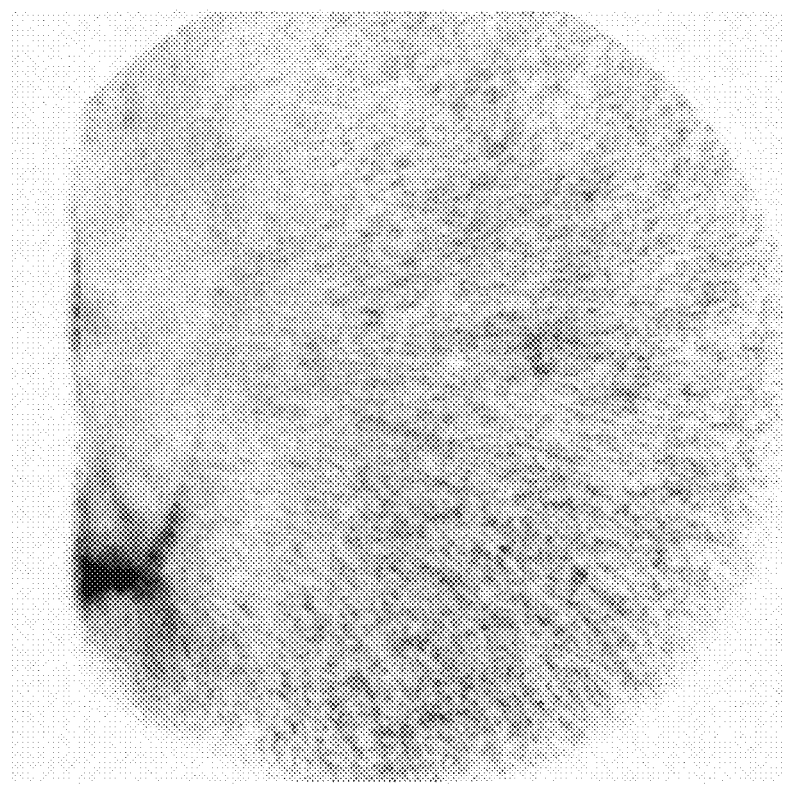
FIG. 3B is an image depicting the green fluorescence protein (GFP) emission during ultrasound exposure using florescence microscopy.
Figure 3C:
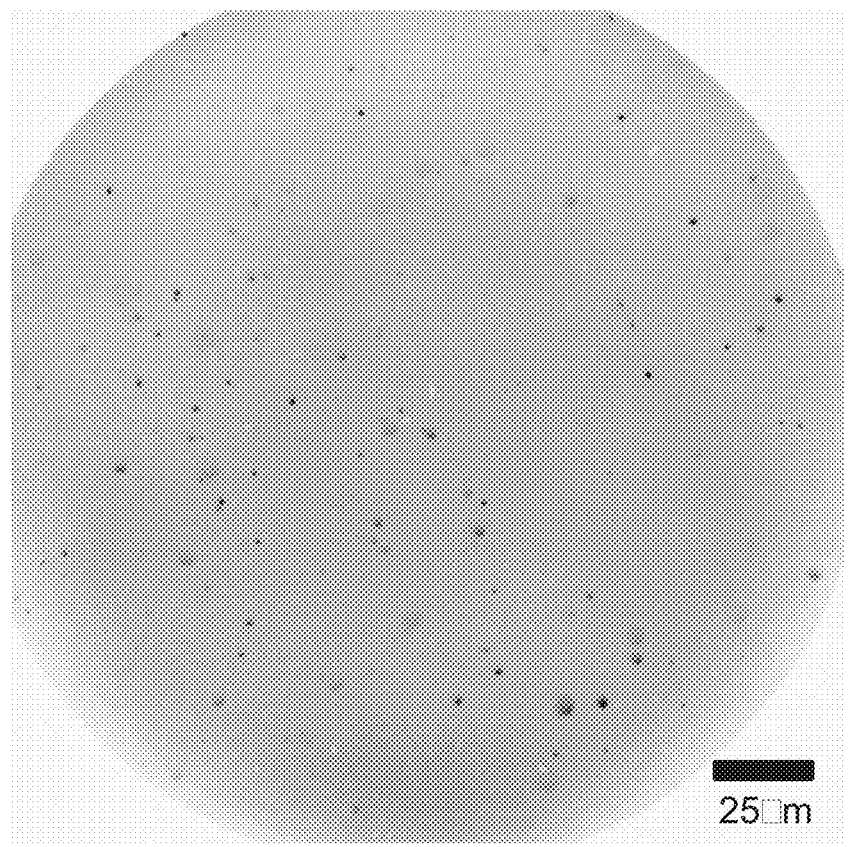
FIG. 3C is an image depicting the green fluorescence protein (GFP) emission after ultrasound exposure using florescence microscopy.
Figure 4A:
FIG. 4A is bright field microscopy image of the bacteria before exposure.
Figure 4B:
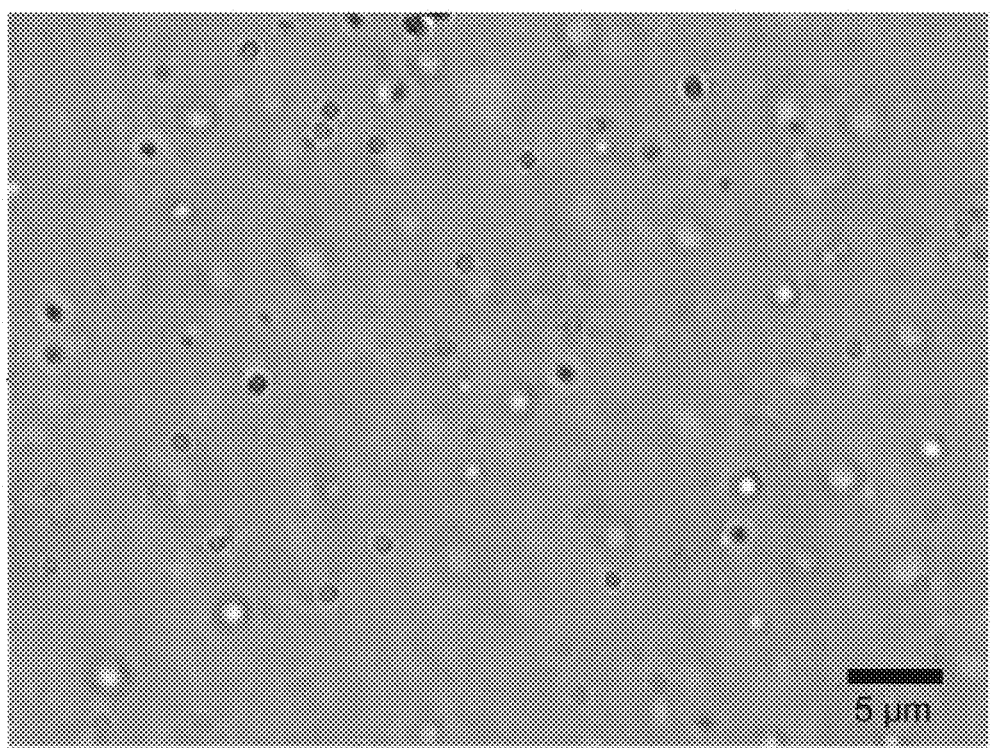
FIG. 4B is a bright field microscopy image of the bacteria after exposure.

The effect of cavitations on the integrity and fluorescence emission of the cells was demonstrated. FIG. 3A is an image 300a depicting the green fluorescence protein (GFP) emission before ultrasound exposure using florescence microscopy. FIG. 3B is an image 300b depicting the green fluorescence protein (GFP) emission during ultrasound exposure using florescence microscopy. FIG. 3C is an image 300c depicting the green fluorescence protein (GFP) emission after ultrasound exposure using florescence microscopy. The images in FIGS. 3A to 3C have been inverted. The original fluorescence images are inverted and shown in FIGS. 3A to 3C to improve clarity for illustration purposes. FIG. 4A is bright field microscopy image of the bacteria before exposure. FIG. 4B is a bright field microscopy image of the bacteria after exposure. FIGS. 4A and 4B are zoomed in images showing that after ultrasound (US) treatment, the rod-shaped *E. coli* cells are broken into fragments.

The images in FIGS. 3A-C and FIGS. 4A-B were captured with a camera connected to a microscope and a long working distance objective lens with 100× magnification and 1.0 mm correction for the glass substrate (LCPLFL-LCD 100×, Olympus). The depth of focus of the objective is 0.79 µm, which is much shorter than the microchannel height of 20 µm. Ultrasound (US) is applied for 389 ms at a frequency of 128.7 kHz using a driving voltage of 200 V; the duration corresponds to 50 000 US cycles. FIG. 3A depicts a population of intact GFP-fluorescent bacterial cells with a dark non-fluorescing background prior to US exposure. During the exposure, the cavitation bubbles create such intense mixing that images of cells are motion blurred (FIG. 3B). The intense mixing also causes the cells move out of the focal plane, making it difficult to resolve the history of cell translation during the US exposure. Shortly after the US exposure, when the flow has ceased, the effect on the cells becomes apparent (FIG. 3C). Besides a greenish supernatant, no intact bacteria remains, indicating the US exposure has completely lysed the cells thus releasing the intracellular GFP into the liquid medium as the cells are effectively disrupted. Further checks along the microchannel 202a do not reveal any intact GFP-fluorescent cells within the channel 202a. To further examine the integrity of the treated cells, high magnification images were also taken before and after the US exposures under bright field illumination. FIG. 3B depicts the complete fragmentation of the rod-shaped cells into small fragments. The fragmentation may be attributed to the fluid mechanic forcing, i.e. shear stress generated from the oscillating cavitation bubbles.

Figure 5:
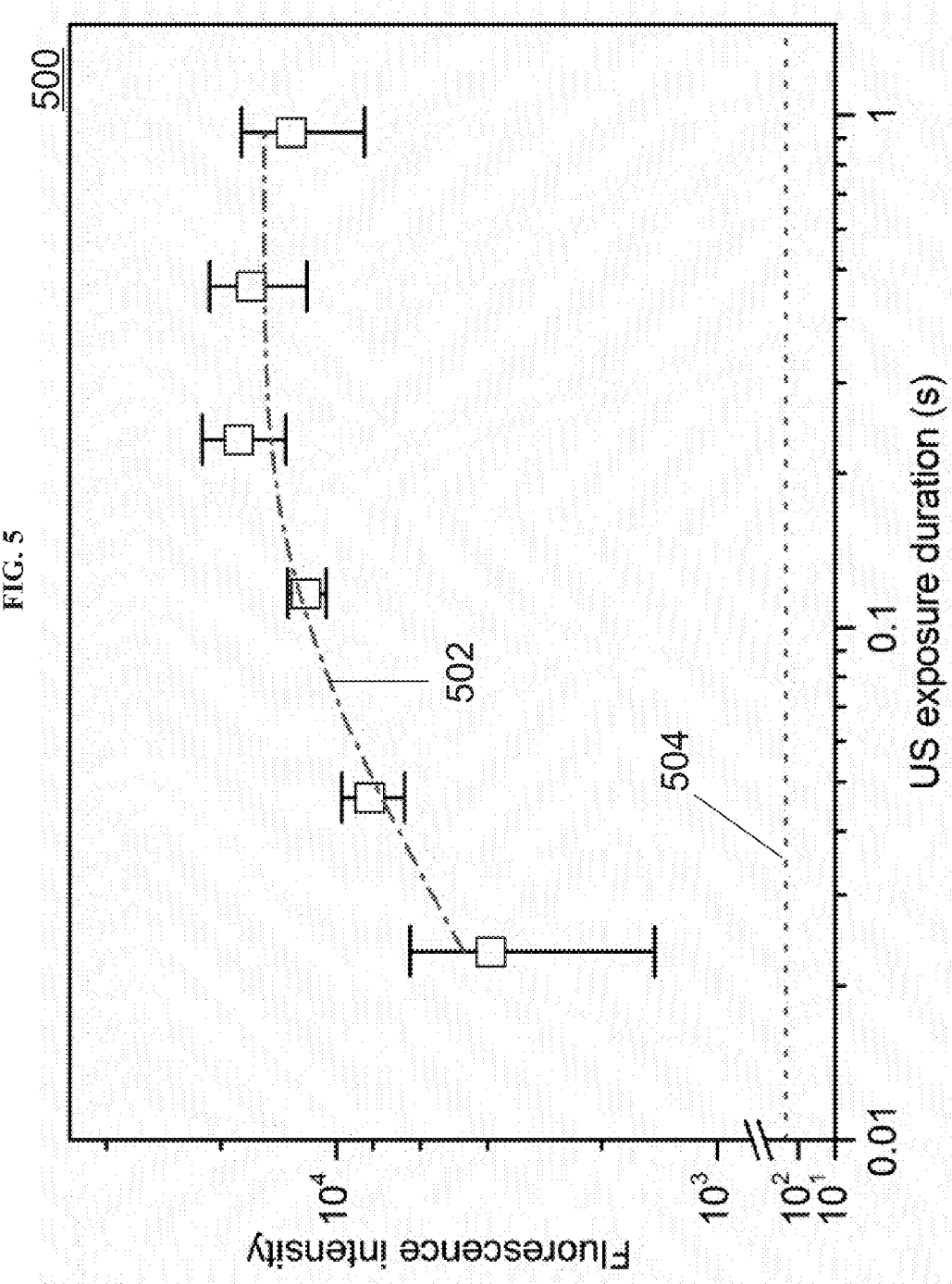
FIG. 5 is a graph of florescence intensity against ultrasound (US) exposure duration (in seconds).

The amount of intracellular proteins released to the supernatant can be determined by measuring the fluorescence of the GFP protein at its corresponding emission wavelength of 509 nm. FIG. 5 is a graph 500 of florescence intensity against ultrasound (US) exposure duration (in seconds). The line 502 shows the measured fluorescence intensity in the clarified supernatant from *E. coli* samples after the ultrasound treatment at different exposure durations. The dashed negative control line 504 corresponds to the fluorescence intensity of the untreated sample. Line 502 shows a significant increase in the fluorescence after a short US exposure of approximately 20 milliseconds. The fluorescence increases with exposure duration reaching a plateau in less than 1 second of US exposure.

Figure 6:
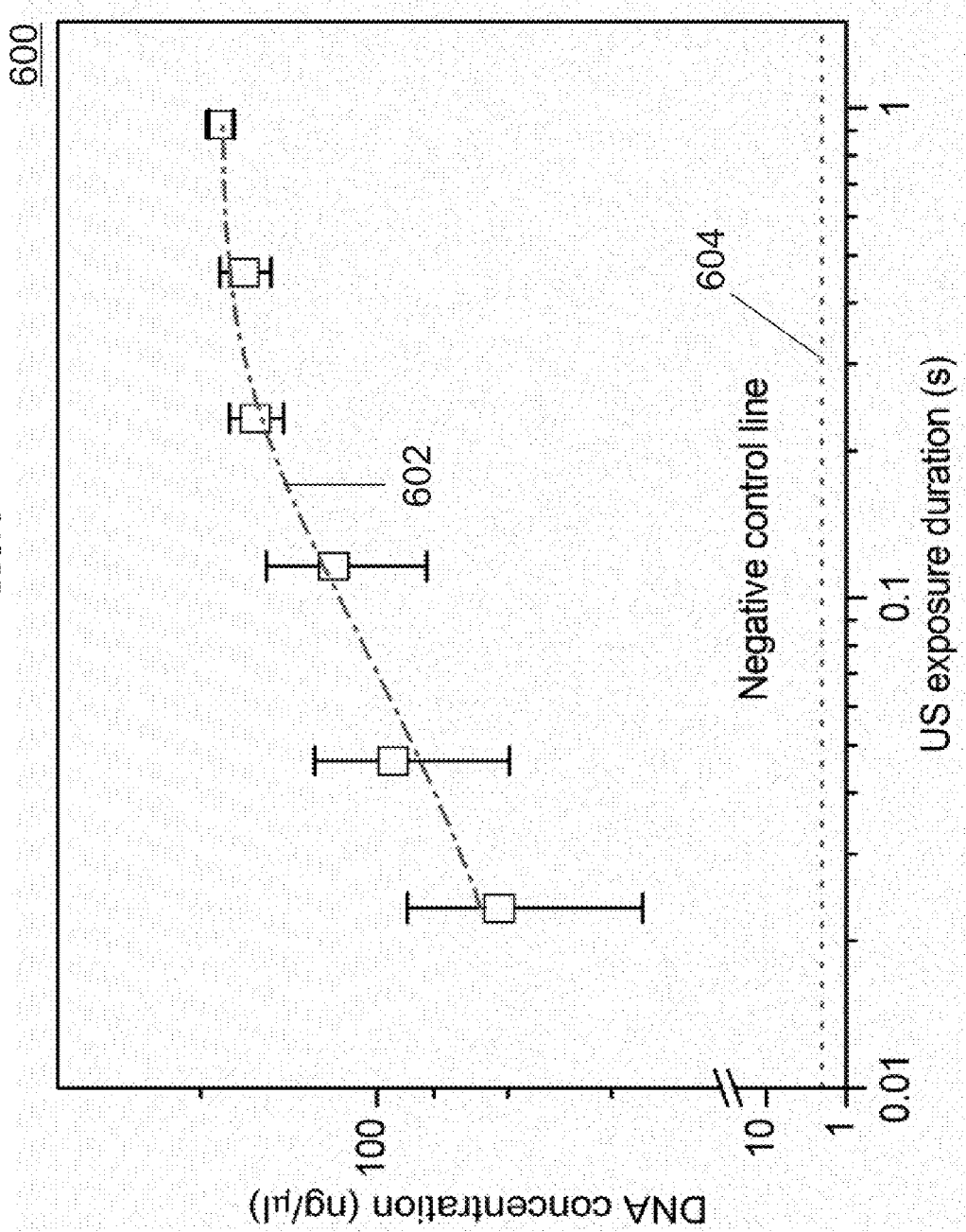
FIG. 6 is a graph of DNA concentration (in nanograms per microliter) against ultrasound (US) exposure duration (in seconds).

As cells undergo ultrasound-mediated lysis, nucleic acids and other cytoplasmic molecules will also be released into the medium. Hence, another alternative method to assess for efficient cell lysis is by performing qRT-PCR to quantify the amount of genomic DNA released into the supernatant. FIG. 6 is a graph 600 of DNA concentration (in nanograms per microliter) against ultrasound (US) exposure duration (in seconds). FIG. 6 shows the results of qRT-PCR analysis of the same samples shown in FIG. 4 using a pair of primers targeting *E. coli* 16SrDNA. Line 602 shows a sample treated with ultrasound while line 604 shows a control sample without being subjected to ultrasound. The data points with error bars used to plot line 602 are obtained from multiple runs (2-4 runs). The line 604 is obtained from the average DNA concentration of the untreated samples from various batches.

As expected, a significantly higher amount of DNA was detected in the treated samples (shown in line 602) compared to the untreated samples (negative control shown in line 604). The trend of increasing DNA concentration over the exposure duration is similar to that of fluorescence intensity (FIG. 4). As more cells are lysed due to the longer ultrasound exposure, more nucleic acids are released to the supernatant, resulting in higher DNA concentration. As before, the DNA concentration also reaches a plateau approximating the maximum theoretical genomic DNA yield within 1 second of exposure. The plateau is believed to relate to an extensive lysis of nearly all cells in the sample, which was also visually confirmed by the fluorescence microscopy images shown in FIGS. 3A-C and FIGS. 4A-B. It may be argued that a built up of cavitation activity leads to a change of the acoustic impedance which reduces the transmission of acoustic energy. Yet, only a small area fraction of the radiating glass plate is covered with cavitation bubbles, and the cavitation activity is still observed even after many cycles of ultrasound exposure. Thus, the plateau may not be explained by mechanical causes, for example due to a drift of the system's resonance frequency.

*Pichia pastoris* is a species of yeast cells with diameters of approximately 4 μm (comparable to the length of *E. coli* bacteria), but their shape is elliptical or oval in contrast to the rod-shaped bacteria. Yeast cells have a rigid extracellular cell wall consisting of a layered mesh of embedded glucans, chitin and mannoproteins which provides physical protection and gives structural strength to the cells. The bursting strength of yeasts measured using micromanipulation methods was found to be at least an order of magnitude higher than typical animal cells. Hence, *Pichia pastoris* can be regarded as comparatively tough cells to lyse.

Figure 7A:
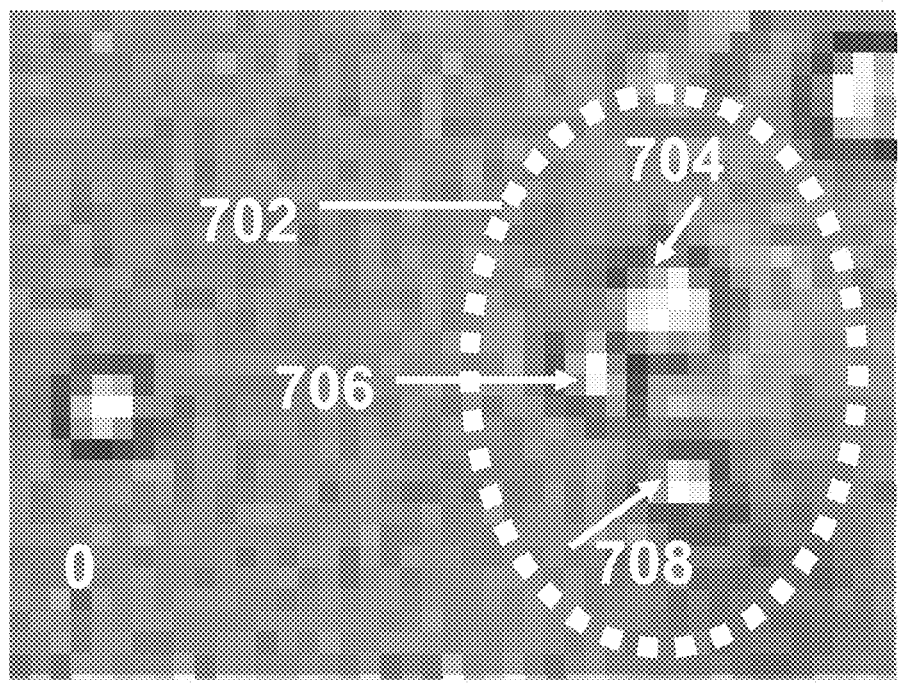
Figure 7B:
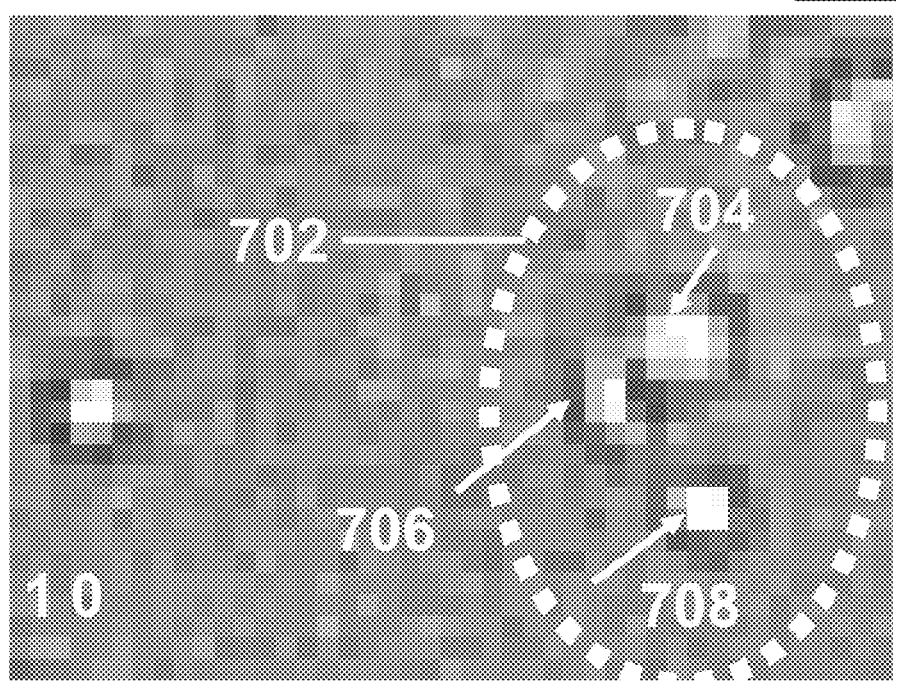
Figure 7C:
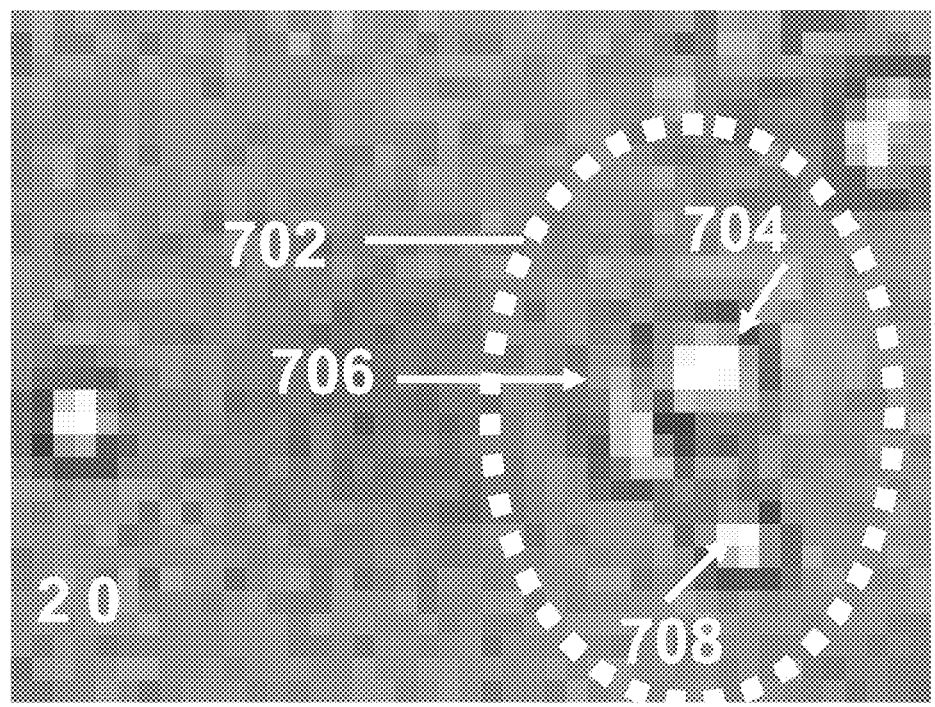
Figure 7D:
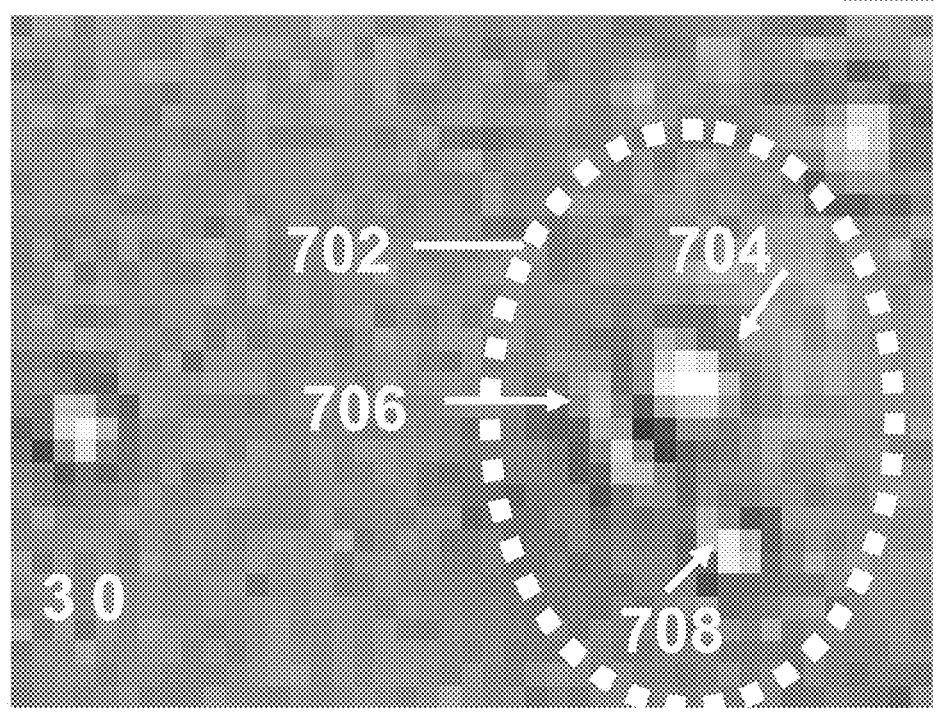
Figure 7E:
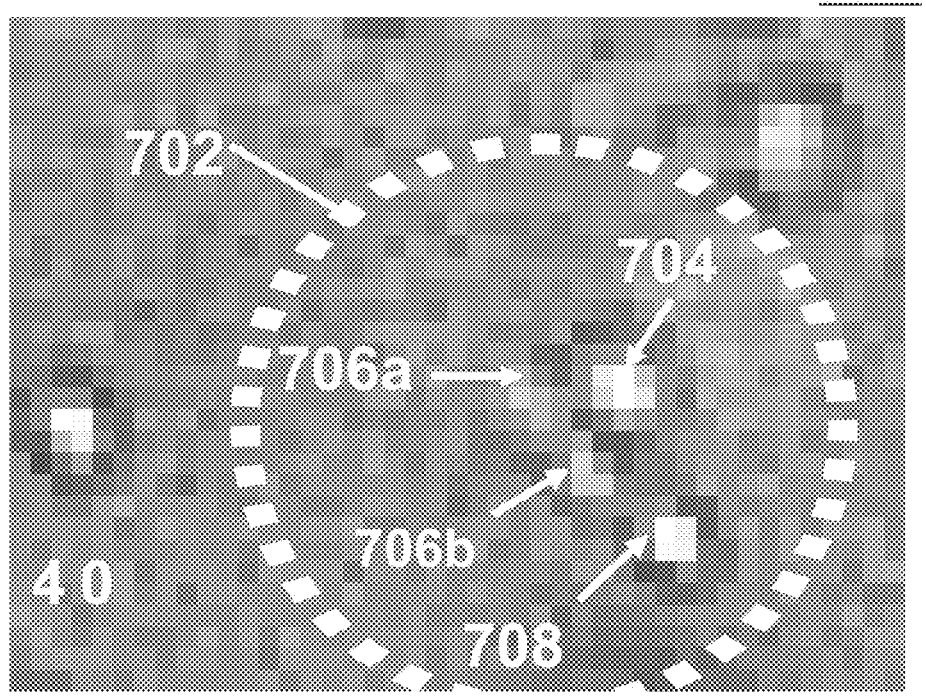
Figure 7F:
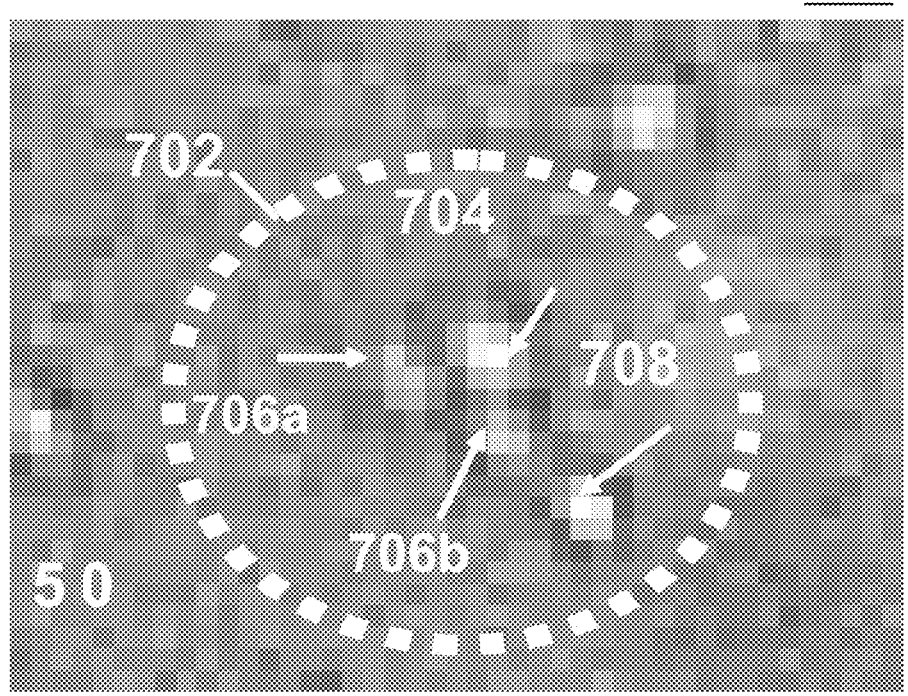

FIGS. 7A-F are a high speed sequence of images showing the deformation and disruption of the yeast cells when they are exposed to the US vibration. The numbers of the bottom left of the images show the time lapsed (in microseconds) since the cells are exposed to ultrasound. FIG. 7A is an image 700a including a group of cells 702 just prior to ultrasound (US) exposure. The group of cells 702 (including cells 704, 706 and 708) is near the bubble during ultrasound exposure and is herein shown to illustrate bubble-cells interaction. Soon after the ultrasound is applied (at t=0 μs), cavitation is observed in the microchannel. No bubbles are visible in FIGS. 7A-F as cavitation bubbles are close to their minimum size. This allows the capturing of a clearer view of the cells as they are moved and deformed (stretched) by a straining flow. FIG. 7B is an image 700b of the group of cells 702 10 μs since ultrasound (US) exposure. FIG. 7C is an image 700c of the group of cells 702 20 μs since ultrasound (US) exposure. FIG. 7D is an image 700d of the group of cells 702 30 μs since ultrasound (US) exposure. FIG. 7E is an image 700e of the group of cells 702 40 μs since ultrasound (US) exposure. FIG. 7F is an image 700f of the group of cells 702 50 μs since ultrasound (US) exposure.

FIGS. 7A-F show cell 706 experiences a particularly strong deformation. Initially (t=0 μs), cell 706 as a round shape with a diameter of 3-4 μm. The cell 706 becomes stretched at t=20 μs. At t=40 μs, the cell 706 splits into two fragments 706a, 706b as a result of high shear stress of the oscillating bubbles. Presumably, cells in the microchannels can become stretched above their yield strength and then rupture. This may consequently result in leakage of intracellular content into the supernatant.

Figure 8:
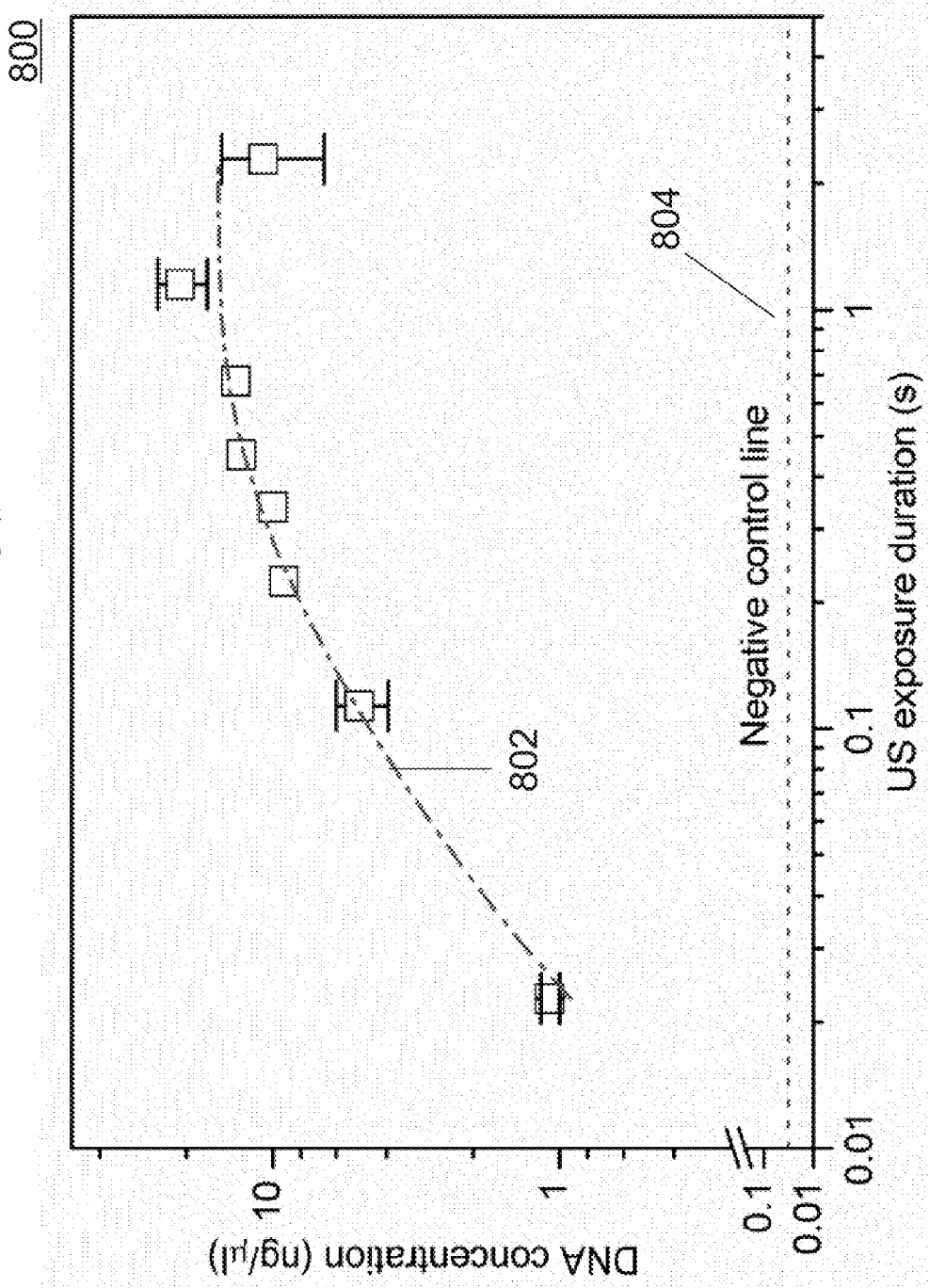
FIG. 8 is a graph of DNA concentration (in nanograms per microliter) against ultrasound (US) exposure duration (in seconds).

The DNA released from *P. pastoris* was quantified using qRT-PCR analysis. FIG. 8 is a graph 800 of DNA concentration (in nanograms per microliter) against ultrasound (US) exposure duration (in seconds). The amount of DNA is plotted as a function of US exposure duration double-logarithmically. Line 802 shows a sample treated with ultrasound while line 804 shows a control sample without being subjected to ultrasound. The data points with error bars used to plot line 802 are obtained from multiple runs (2-4 runs). The line 804 is obtained from the average DNA concentration of the untreated samples from various batches. Line 802 shows the DNA concentration, thus the number of disrupted cells, increases with US exposure duration and levels off at a US exposure duration of about 1 second. This plateau indicates that majority of the cells have lysed. Any further increase in the exposure duration in our experiments consistently leads to a slight decrease in the DNA concentration. This may be explained by mechanical or chemical damage of the harvested DNA, e.g. formation of OH radicals from long ultrasound exposure.

Figure 9:
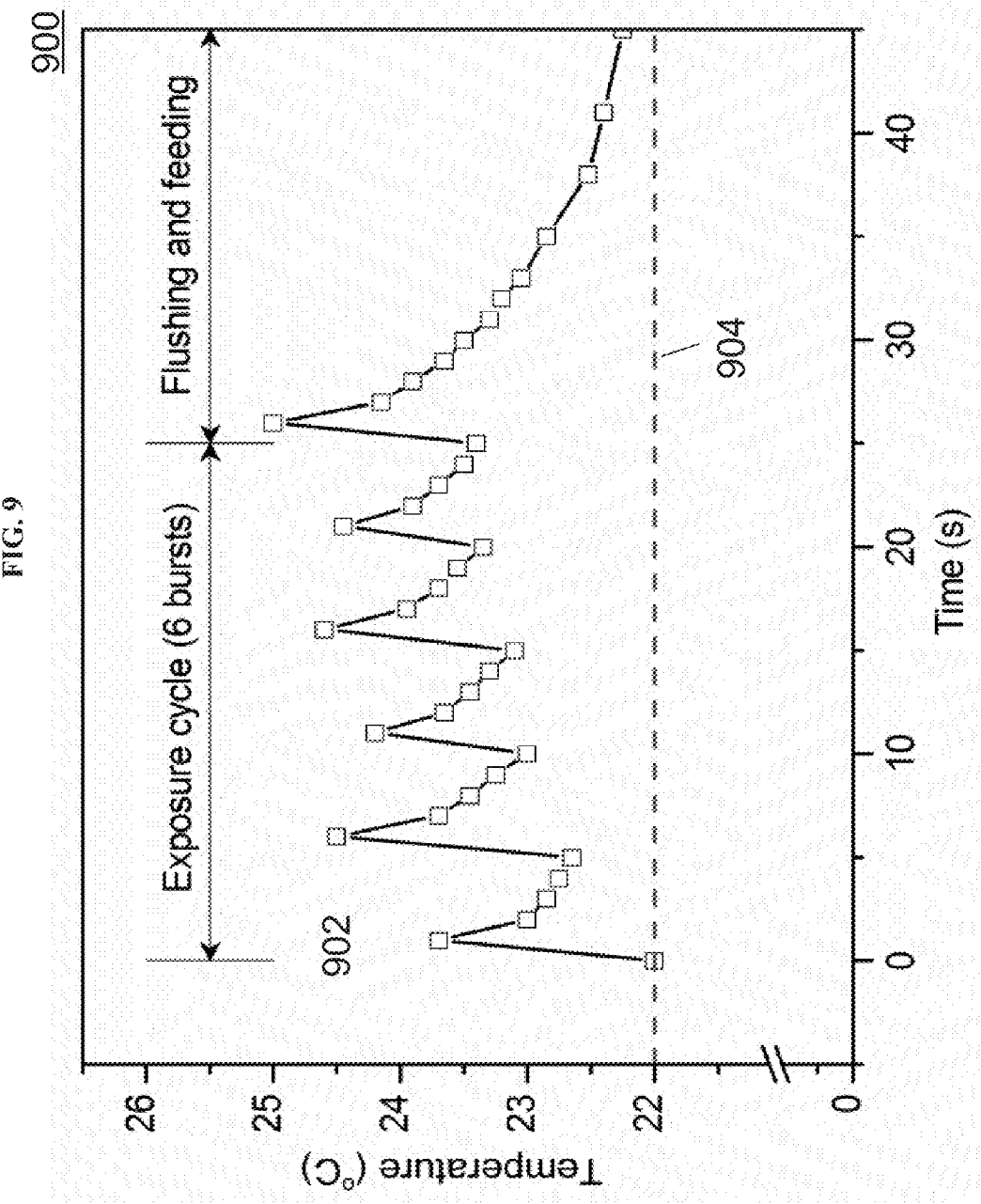
FIG. 9 is a graph illustrating the temperature (in ° C.) against time (in seconds).

One ever present concern of ultrasound usage for cell lysis is the heating of the cells and their subsequent denaturation of proteins which may affect downstream bio-assays. In one protocol, six short bursts of US are applied with a time interval between the bursts to allow cooling of the sample. FIG. 9 is a graph 900 illustrating the temperature (in ° C.) against time (in seconds). Line 902 tracks the changes in temperature of the sample over a cycle of ultrasound exposure. The values were obtained from the average of two temperatures at two different locations on the channels. The first temperature is obtained near a piezoelectric transducer while the second temperature is obtained near the middle of the microfluidic device. Line 904 marks the initial temperature just prior ultrasound exposure. The temperature is measured with a type K thermocouple introduced through small holes into the microchannel. The measurements are carried out for ultrasound exposures with a total duration of 0.92 seconds (6 bursts of 0.154 seconds), which corresponds to 6×20 000 ultrasound cycles at a driving frequency of 130 kHz. During the measurement, the same sample is kept in the channel to monitor the changes in temperature. As shown earlier in our examples, this exposure parameter may be sufficient for complete lysis of both bacteria and yeast. Each burst of ultrasound gives rise to a temperature increase of only 1-2° C. The time delay between the bursts allows the temperature of the sample to cool down by 1.0-1.5° C. Hence, for the full ultrasound exposure treatment, the maximum temperature increase of the sample remains below 3.3° C.

Figure 10A:
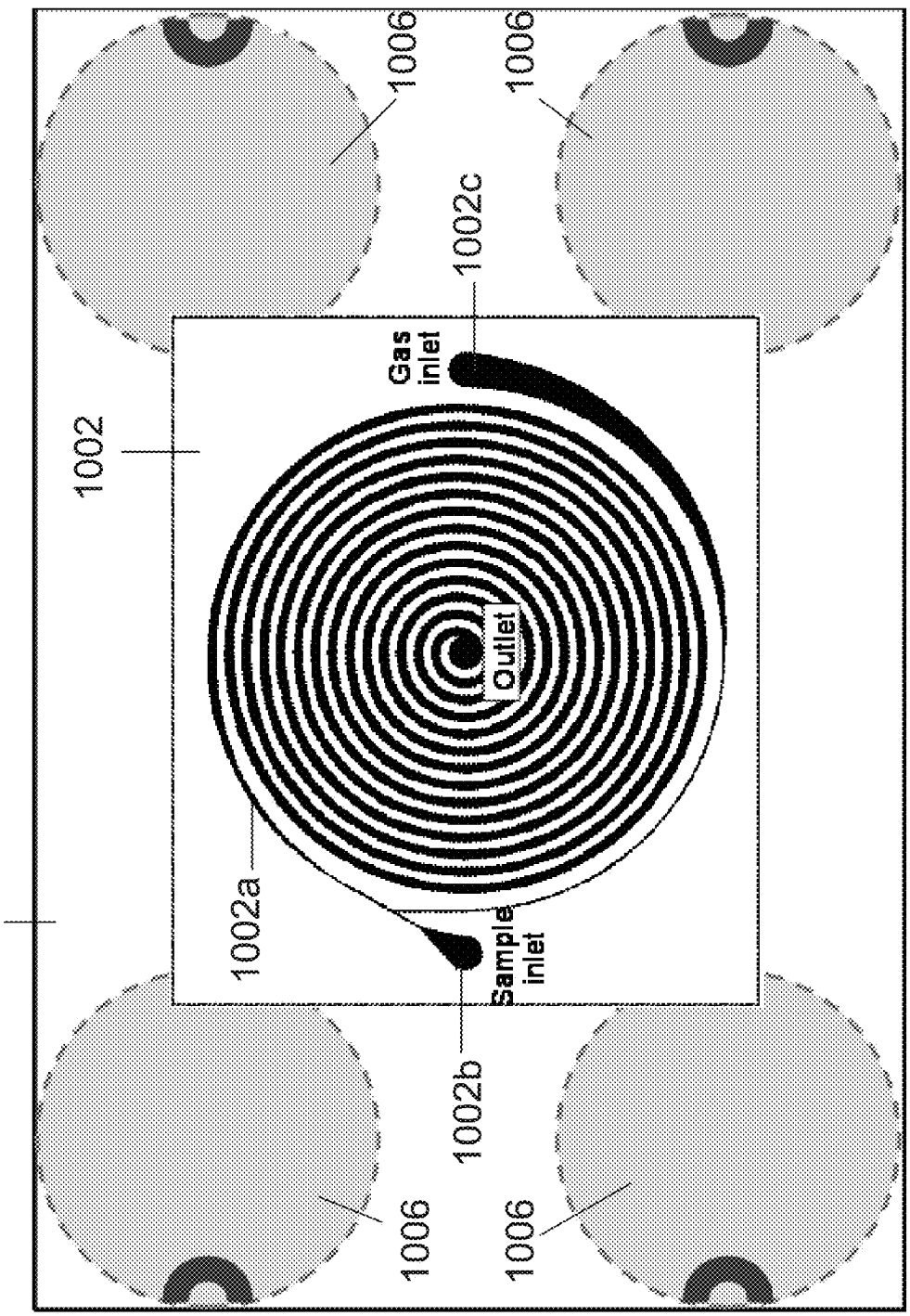
FIG. 10A shows a schematic of another setup according to various embodiments.
Figure 10B:
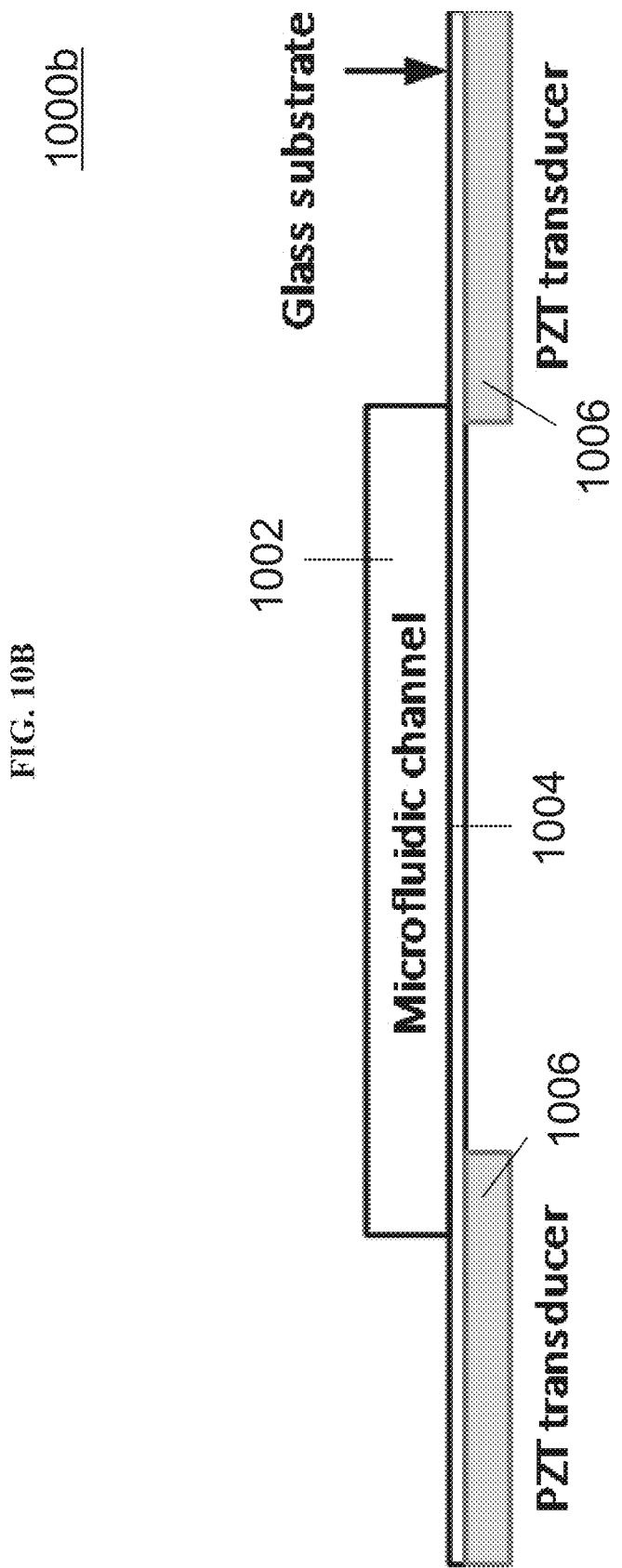
FIG. 10B shows a side view of the setup in FIG. 10A according to various embodiments.

FIG. 10A shows a schematic 1000a of another setup according to various embodiments. FIG. 10B shows a side view 1000b of the setup in FIG. 10A according to various embodiments. The setup may be configured for lysis of endospores. The setup may include a microfluidic device 1002. The microfluidic device 1002 may include a main channel 1002a. The microfluidic device 1002 may further include an inlet channel 1002b and a further inlet channel 1002c. The main channel 1002a, the inlet channel 1002b and the further inlet channel 1002c may form a Y-junction. The inlet channel 1002b may be configured to transport sample including biological material in a liquid to the main channel 1002a. The further inlet channel 1002c may be configured to carry gas to the main channel to form a liquid-gas interface. The main channel 1002a, the inlet channel 1002b and the further inlet channel 1002c may be on a substrate 1004. The substrate 1004 may be a glass substrate. In various alternate embodiments, the substrate 1004 may include silicon or polydimethylsiloxane (PDMS). The channels 1002a, 1002b and 1002c have divergent shape toward the inlets to minimize the possibility of liquid sample reaching back the inlet ports when the gas pressure is reduced. The setup may further include one or more transducers 1006. The one or more transducers may be on or under the substrate 1004.

Figure 10C:
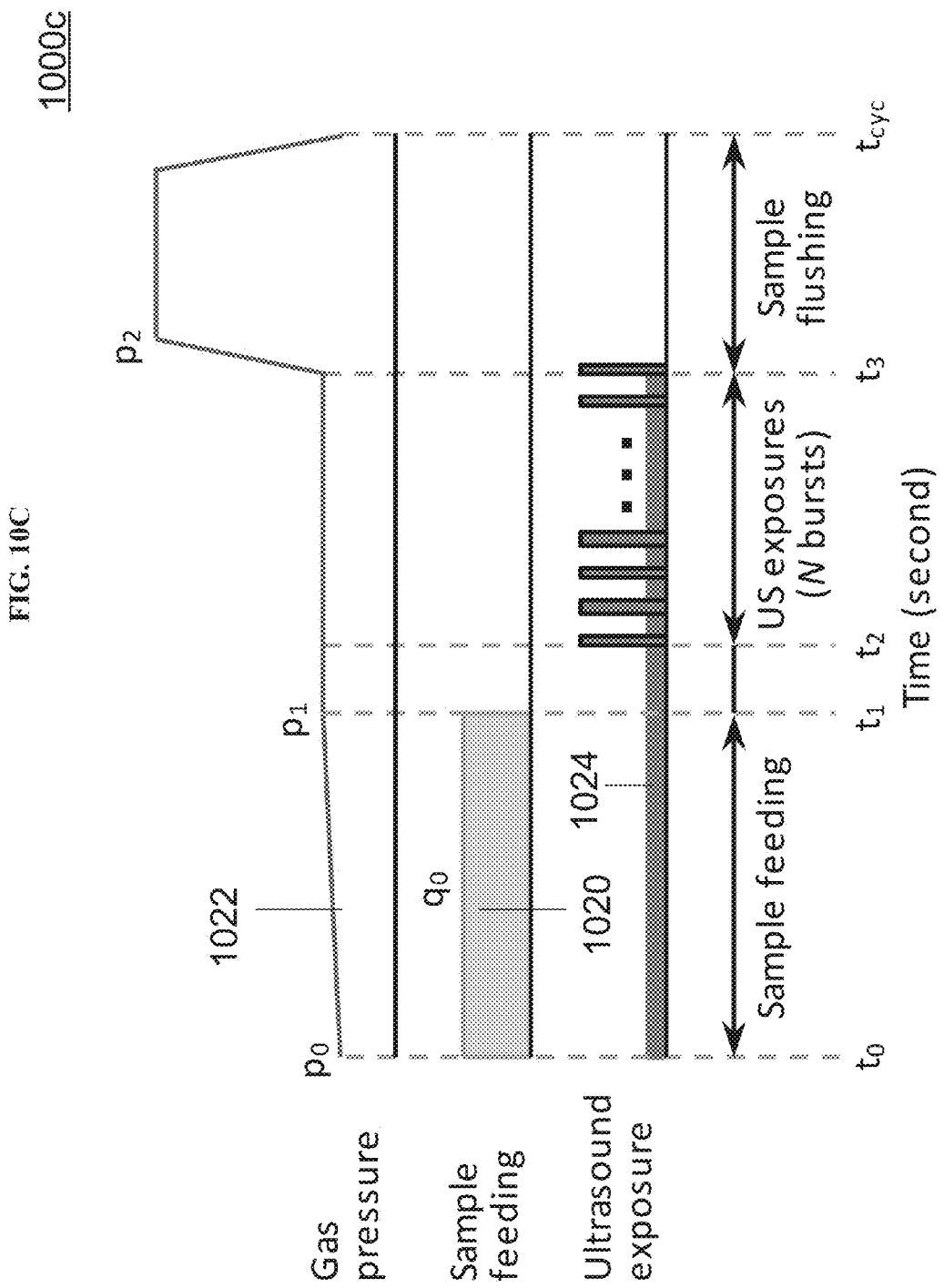
FIG. 10C is a timing diagram illustrating the timings of sample feeding, the acoustic wave exposure and variation of pressure.

FIG. 10C is a timing diagram 1000c illustrating the timings of sample feeding, the acoustic wave exposure and variation of gas pressure. In various embodiments, flowing or feeding of the sample, applying the acoustic waves and/or flowing or providing the gas may be controlled automatically. In one example, at 1020, five microliters of endospore suspension (*Bacillus subtilis*) is injected into the microchannel 1002b at a flowrate of $q_0$ (e.g. 6 μl/min), while at the same time, at 1024, the transducers 1006 are excited at a low driving voltage of 20 V (at 1024) to entrap gas as the liquid moves along the channels 1002b, 1002a. The gas pressure is slowly increased, at 1022, during the sample injection 1020 from $p_0$ to $p_1$ (e.g. 0.2 bars to 0.4 bars at 1022) to prevent the liquid sample from moving toward the gas inlet (coupled to the gas inlet channel 1002c) and also to create gas/liquid slugs along the channel 1002a. The lower pressure $p_0$ should be sufficiently high to prevent the liquid sample to enter the gas inlet channel 1002c, while the higher pressure $p_1$ should be lower than the total pressure losses along the channel 1002a so that the liquid are kept within the channel 1002a during sample feeding. The gas pressure is then maintained at $p_1$ for a short duration (e.g. ~10 seconds) to allow the pressure in the channel 1002a to stabilize. The sample is subsequently exposed to up to 64 bursts of ultrasound every 5 seconds by an amplifier (AG1021, LF Amplifier/Generator, T&C Power Conversion, not shown in FIGS. 10A, 10B) at a driving voltage of 200 V with 10% duty cycle. Each burst is composed of a harmonic driving of 0.5 seconds of ultrasound of 200 V amplitude at the resonance frequency of the microfluidic device 1002. After the ultrasonic exposures, the sample is flushed out of the channel 1002a by increasing the gas pressure to $p_2$ (e.g. 1 bar) for a certain time duration ($t_{cyc}$–$t_3$). The cycle is then repeated until a sufficient amount of the sample is collected for downstream bioassays (plate-count and qRT-PCR), typically about 40-60 μl.

Figure 10D:
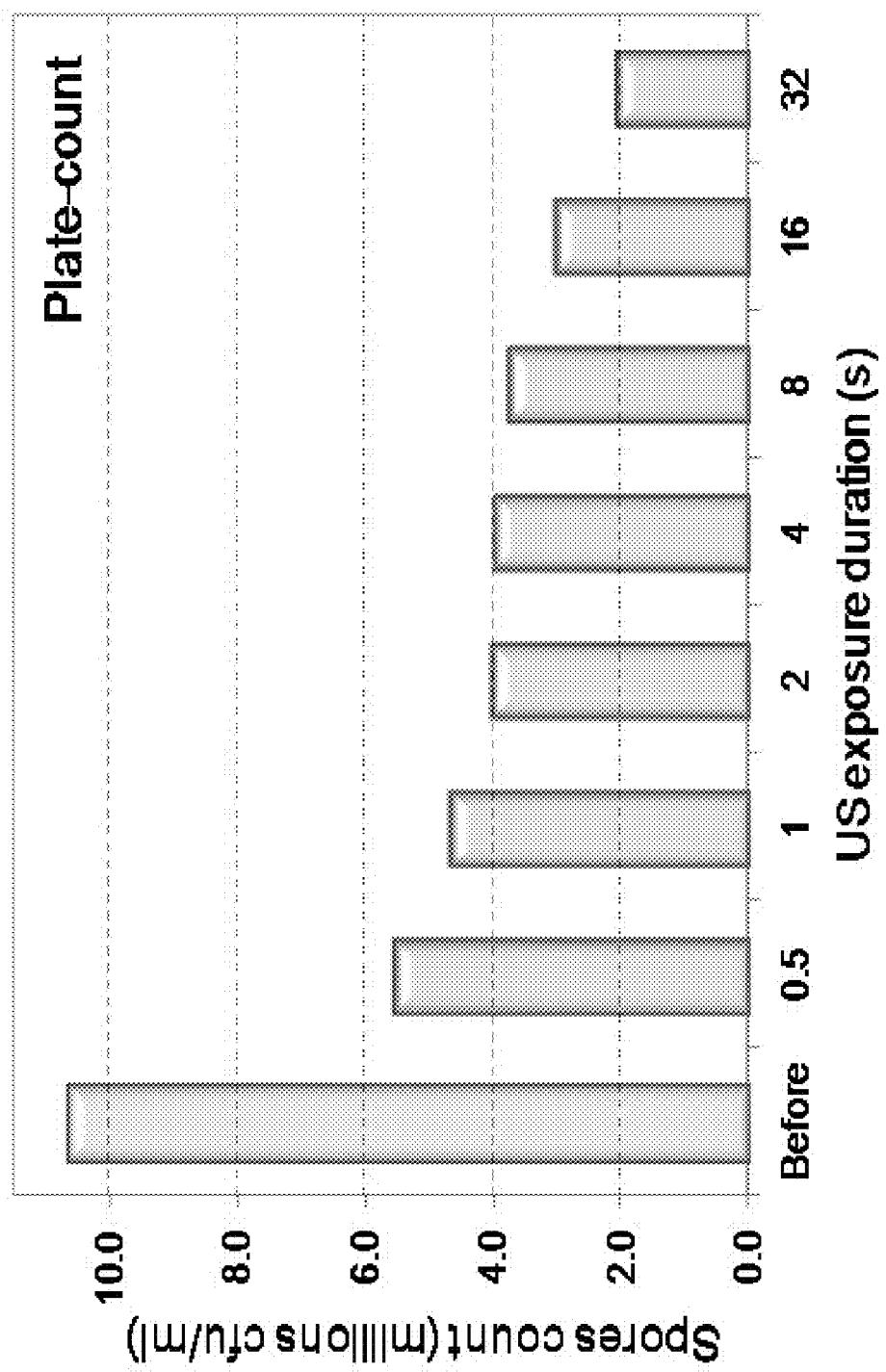
FIG. 10D is a graph of the spore count (millions colony-forming units (cfu) per milliliters) against ultrasound exposure (seconds).
Figure 10E:
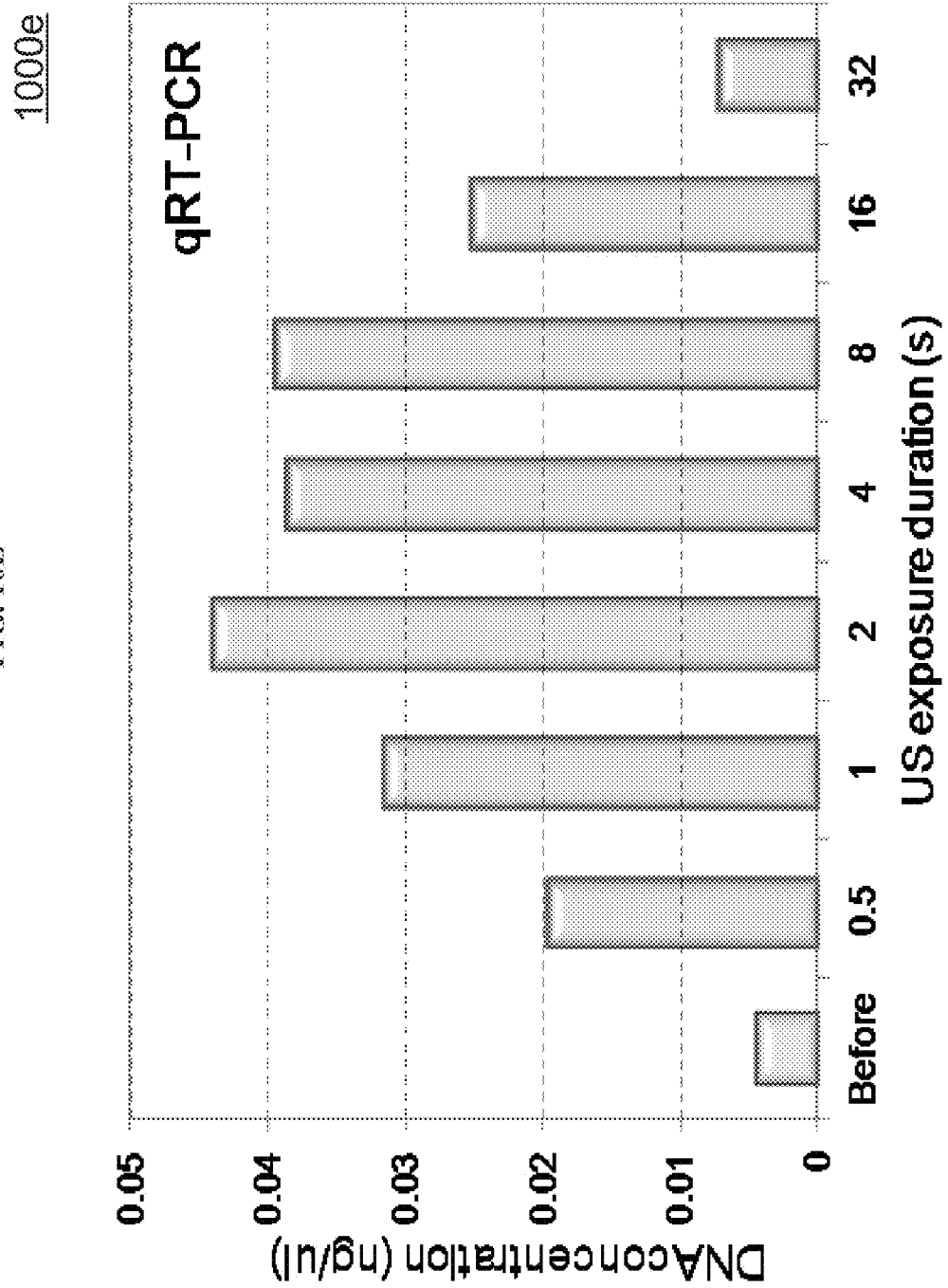
FIG. 10E is a graph of the DNA concentration (nanograms per microliter) against ultrasound exposure (seconds).

FIG. 10D is a graph 1000d of the spore count (millions colony-forming units (cfu) per milliliters) against ultrasound exposure (seconds). FIG. 10E is a graph 1000e of the DNA concentration (nanograms per microliter) against ultrasound exposure (seconds). The results in FIGS. 10D and 10E are obtained from the average of three sets of experiments. The plate-count (FIG. 10D) shows a significant decrease of intact spores after 0.5 seconds of ultrasound (US) exposures. At least half of the spores are lysed. As the ultrasound exposure duration increases, the number of intact cells also decreases. After 32 seconds of US exposure, only 20% of the spores are intact.

FIG. 10E shows the DNA concentration of the treated samples. As the spores are lysed, nucleic acids are released into the medium. The amount of DNA released into the supernatant increases with longer US exposure duration until 2 seconds, and it subsequently becomes almost constant until 8 seconds. Further increase of the exposure duration causes fragmentation and an apparent drop in DNA concentration.

Various embodiments provide the ability to lyse microliters volume of cells without generation of excess heat, hence maintaining the quality of the harvested intracellular contents. This may be achieved by exposing the cells to a controlled amount of cavitation for sufficiently short times. In various embodiments, the large surface area due to the microfluidic environment may enhance the transport of heat quickly away from the liquid.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A method of breaking down biological material, the method comprising:
    providing a sample into a channel disposed on a substrate, the sample comprising the biological material in a liquid;
    providing a gas into the channel such that the gas forms an interface with the liquid; and
    exciting a transducer attached to the substrate to generate and apply acoustic waves in a plurality of sequential bursts to the interface to break down the biological material.

2. The method according to claim 1, wherein cavitations are generated by oscillations when the acoustic waves are applied to the interface; and
    wherein the cavitations are configured to break down the biological material.

3. The method according to claim 1, wherein the biological material are broken down into biological material fragments.

4. The method according to claim 3, the method further comprising:
    detecting the biological material fragments.

5. The method according to claim 3, the method further comprising:
    increasing pressure of the gas to flush the biological material fragments.

6. The method according to claim 5, the method further comprising:
    decreasing the pressure of the gas after flushing the sample comprising the biological material fragments.

7. The method according to claim 5, the method further comprising:
    providing a subsequent sample comprising a subsequent biological material after flushing the sample comprising the biological material fragments.

8. The method according to claim 1, wherein a first burst of the plurality of sequential bursts is separated from a second burst of the plurality of sequential bursts by a time interval.

9. The method according to claim 1, wherein the interface is formed in said channel, and said channel is a main channel of a microfluidic device.

10. The method according to claim 9, wherein providing the sample comprises flowing the sample through an inlet channel, the inlet channel in connection with the main channel.

11. The method according to claim 10, wherein providing the gas comprises flowing the gas through a further inlet channel, the further inlet channel in connection with the main channel.

12. The method according to claim 11, wherein the inlet channel is at least substantially perpendicular to the further inlet channel.

13. The method according to claim 9, wherein the main channel comprises a meandering portion.

14. The method according to claim 10, wherein the acoustic wave is at a resonance frequency of the microfluidic device.

15. The method according to claim 1, wherein providing the gas is controlled by a control system.

16. The method according to claim 15, wherein applying acoustic waves is controlled by the control system.

17. The method according to claim 1, wherein the acoustic waves are ultrasound waves.

18. The method according to claim 1, wherein the acoustic waves are generated by one or more piezoelectric transducers.

19. The method according to claim 1, wherein exciting the transducer induces vibration on the substrate to generate the acoustic waves.

* * * * *